(12) United States Patent
Suzuki et al.

(10) Patent No.: US 7,976,523 B2
(45) Date of Patent: Jul. 12, 2011

(54) ABSORBENT PRODUCT WITH NONPERMEABLE SURFACE SHEET

(75) Inventors: Migaku Suzuki, Kanagawa (JP); Reiko Moriya, Kanagawa (JP)

(73) Assignee: Japan Absorbent Technology Institute, Tokyo (JP)

( * ) Notice: Subject to any disclaimer, the term of this patent is extended or adjusted under 35 U.S.C. 154(b) by 221 days.

(21) Appl. No.: 10/538,786

(22) PCT Filed: Dec. 10, 2002

(86) PCT No.: PCT/JP02/12900
§ 371 (c)(1),
(2), (4) Date: Jun. 14, 2005

(87) PCT Pub. No.: WO2004/052257
PCT Pub. Date: Jun. 24, 2004

(65) Prior Publication Data
US 2006/0058769 A1   Mar. 16, 2006

(51) Int. Cl.
*A61F 13/15* (2006.01)
*A61F 13/20* (2006.01)

(52) U.S. Cl. .............................. 604/385.101

(58) Field of Classification Search ............ 604/348, 604/383, 385.08, 385.101, 385.14, 385.19, 604/393–96, 381, 395
See application file for complete search history.

(56) References Cited

U.S. PATENT DOCUMENTS

| | | | | |
|---|---|---|---|---|
| 2,929,379 A | * | 3/1960 | Poulsen | 604/385.01 |
| 3,078,849 A | * | 2/1963 | Morse | 604/368 |
| 3,367,334 A | * | 2/1968 | Testa | 604/370 |
| 3,595,235 A | * | 7/1971 | Jespersen | 604/364 |
| 3,612,054 A | * | 10/1971 | Matsuda et al. | 604/370 |
| 3,886,941 A | | 6/1975 | Duane et al. | |
| 3,929,135 A | * | 12/1975 | Thompson | 604/385.08 |
| 3,989,867 A | * | 11/1976 | Sisson | 428/132 |
| 4,321,924 A | * | 3/1982 | Ahr | 604/378 |
| 4,324,246 A | * | 4/1982 | Mullane et al. | 604/366 |
| 4,341,216 A | * | 7/1982 | Obenour | 604/370 |
| 4,342,314 A | * | 8/1982 | Radel et al. | 604/370 |
| 4,463,045 A | * | 7/1984 | Ahr et al. | 428/131 |
| 4,578,068 A | * | 3/1986 | Kramer et al. | 604/368 |
| 4,610,678 A | * | 9/1986 | Weisman et al. | 604/368 |
| 4,673,402 A | * | 6/1987 | Weisman et al. | 604/368 |
| 4,834,735 A | * | 5/1989 | Alemany et al. | 604/368 |
| 4,846,813 A | | 7/1989 | Raley | |
| 4,888,231 A | * | 12/1989 | Angstadt | 428/213 |
| 4,908,026 A | * | 3/1990 | Sukiennik et al. | 604/378 |

(Continued)

FOREIGN PATENT DOCUMENTS
CA   2255465 A1 * 6/2000

(Continued)

*Primary Examiner* — Melanie J Hand
(74) *Attorney, Agent, or Firm* — Oliff & Berridge, PLC

(57) ABSTRACT

An absorbent product capable of preventing the absorbing rate from significantly lowering with the elapse of time, from the start of use to a final stage when the absorbing capacity of the product reaches a limit, is provided. The absorbent product has a very small re-wet amount. The absorbent product includes a liquid-impermeable surface sheet positioned on the upper side, a liquid-impermeable back sheet positioned on the lower side, and an absorber containing super absorbent polymer to absorb discharged liquid positioned between the surface sheet and the back sheet, wherein a flow passage is provided to allow a part or all of the discharged liquid supplied to the surface sheet to move to a side of the back sheet.

38 Claims, 22 Drawing Sheets

U.S. PATENT DOCUMENTS

| | | | |
|---|---|---|---|
| 5,006,394 A * | 4/1991 | Baird | 428/138 |
| 5,085,654 A * | 2/1992 | Buell | 604/370 |
| 5,147,345 A * | 9/1992 | Young et al. | 604/378 |
| 5,185,009 A | 2/1993 | Sitnam | |
| 5,234,423 A * | 8/1993 | Alemany et al. | 604/385.3 |
| 5,476,457 A * | 12/1995 | Roessler et al. | 604/364 |
| 5,571,096 A * | 11/1996 | Dobrin et al. | 604/383 |
| 5,614,283 A * | 3/1997 | Potnis et al. | 428/131 |
| 5,718,698 A * | 2/1998 | Dobrin et al. | 604/383 |
| 5,810,798 A * | 9/1998 | Finch et al. | 604/378 |
| 5,873,870 A * | 2/1999 | Seitz et al. | 604/385.04 |
| 5,897,544 A * | 4/1999 | Ronnberg | 604/385.19 |
| 5,897,545 A * | 4/1999 | Kline et al. | 604/386 |
| 5,904,673 A * | 5/1999 | Roe et al. | 604/385.3 |
| 5,910,137 A * | 6/1999 | Clark et al. | 604/387 |
| 5,977,430 A * | 11/1999 | Roe et al. | 604/378 |
| 5,997,986 A * | 12/1999 | Turi et al. | 428/138 |
| 6,004,306 A * | 12/1999 | Robles et al. | 604/385.21 |
| 6,010,491 A * | 1/2000 | Roe et al. | 604/385.23 |
| 6,111,163 A * | 8/2000 | McCormack et al. | 604/367 |
| 6,232,521 B1 * | 5/2001 | Bewick-Sonntag et al. | 604/378 |
| 6,627,786 B2 * | 9/2003 | Roe et al. | 604/361 |
| 6,730,067 B1 * | 5/2004 | Nukina et al. | 604/385.01 |
| 2003/0093045 A1 * | 5/2003 | Erdman | 604/367 |

FOREIGN PATENT DOCUMENTS

| | | |
|---|---|---|
| EP | 0 360 285 | 3/1990 |
| EP | 0 861 645 A2 | 9/1998 |
| EP | 945110 A2 * | 9/1999 |
| GB | 2 023 069 A | 12/1979 |
| GB | 2 158 721 A | 11/1985 |
| JP | A 03-251244 | 11/1991 |
| WO | WO 93/19715 | 10/1993 |
| WO | WO 9323000 A1 * | 11/1993 |
| WO | WO 9415563 A1 * | 7/1994 |
| WO | WO 95/00093 | 1/1995 |
| WO | WO 9718785 A1 * | 5/1997 |
| WO | WO 9912502 A1 * | 3/1999 |
| WO | WO 03/041626 A1 | 5/2003 |

* cited by examiner

FIG.1
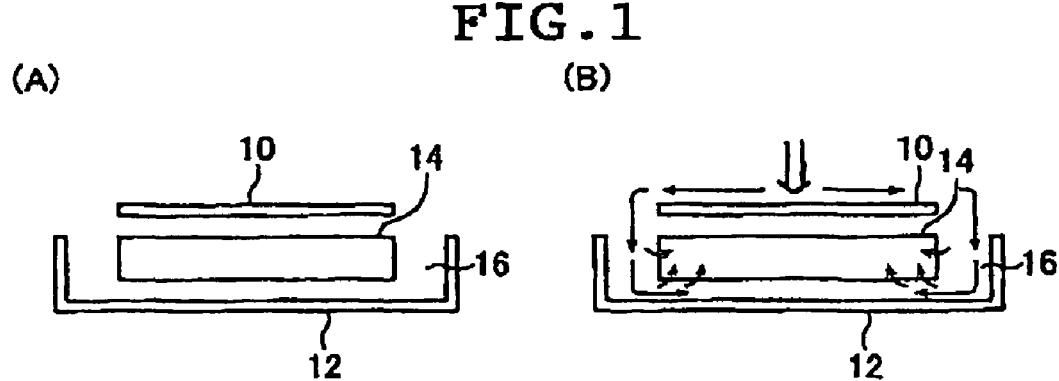
FIG.2
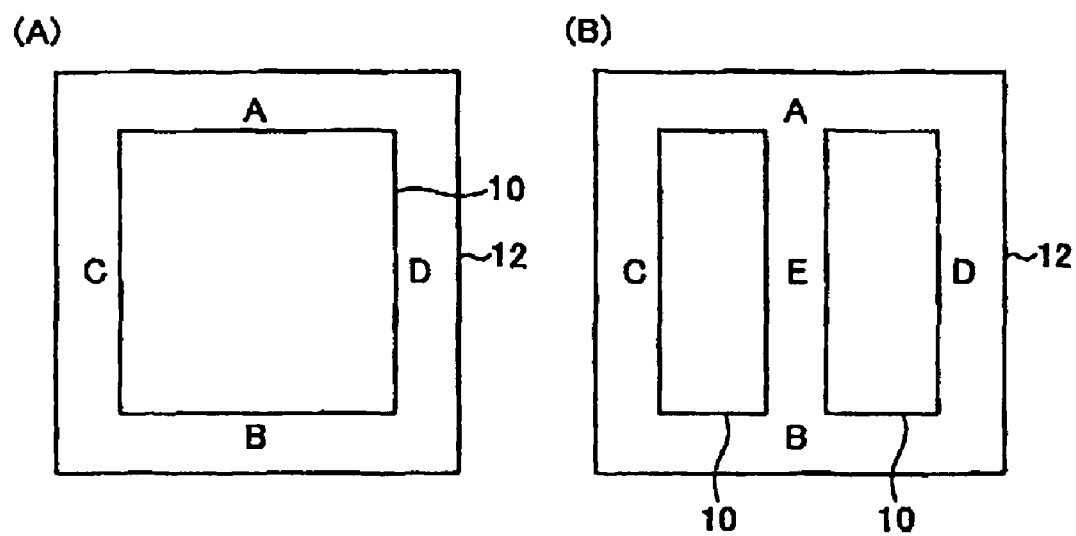
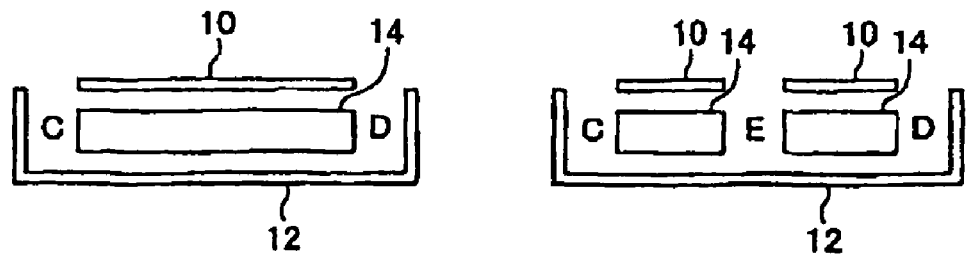

FIG.3
(A)
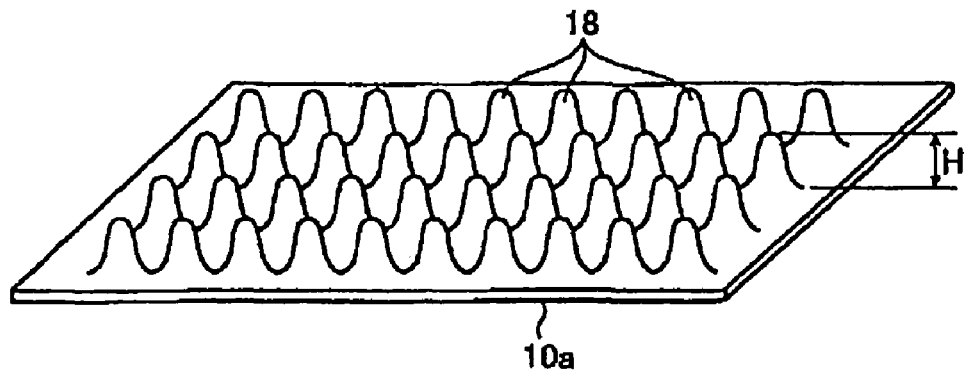
(B)
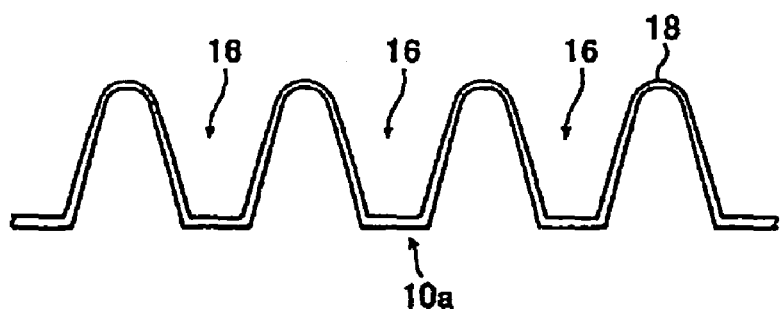
FIG.4
(A)
(B)
(C)
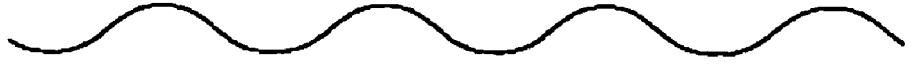
(D)

FIG.5
(A)
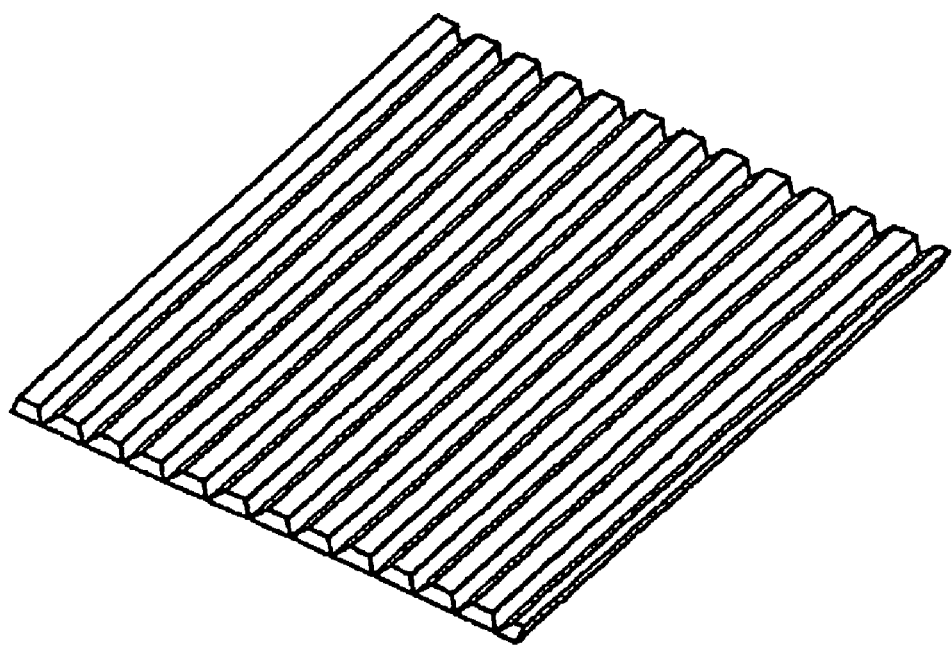
(B)
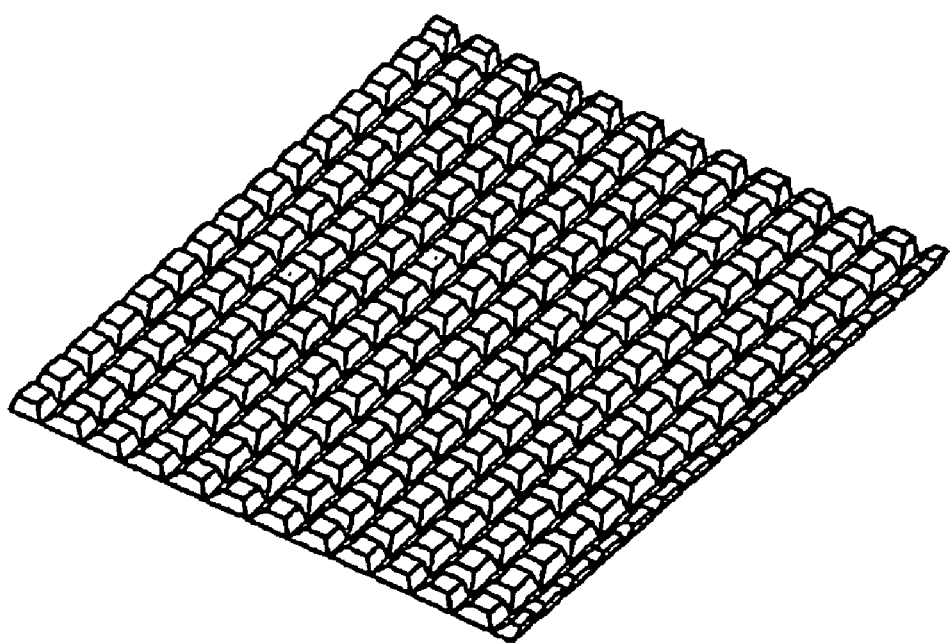

FIG. 9
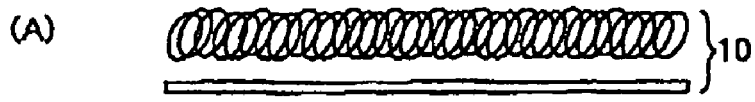
(A)
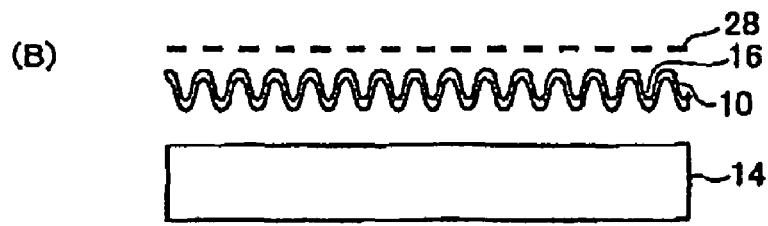
(B)
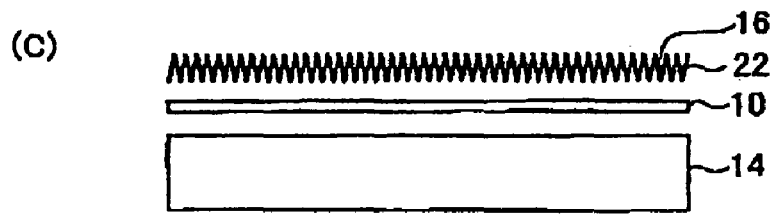
(C)
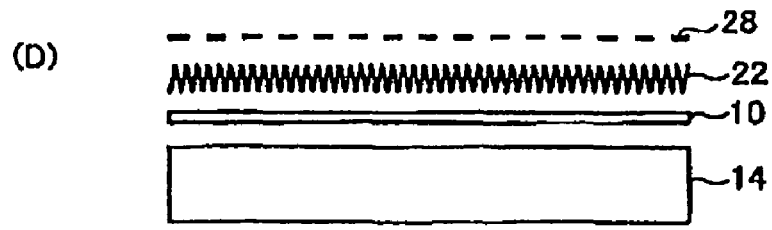
(D)
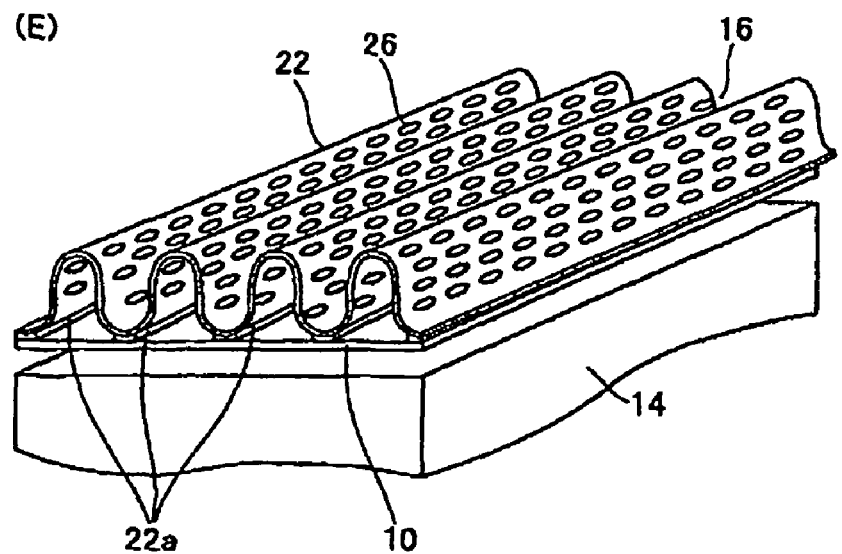
(E)

FIG. 11
(A) 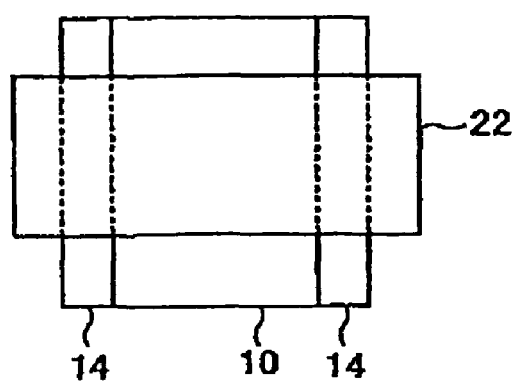
(B) 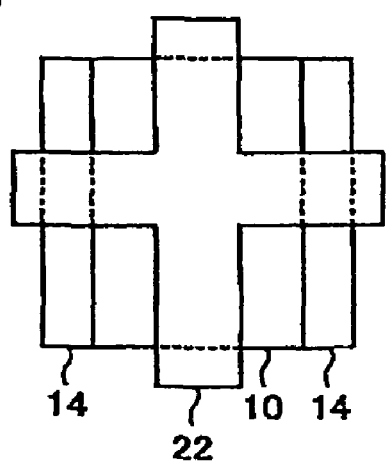
FIG. 12
(A) 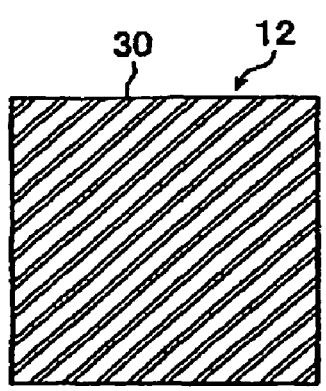
(B) 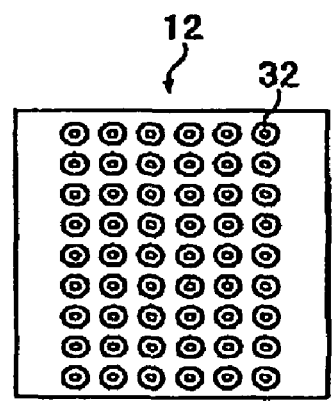

FIG. 13
(A)
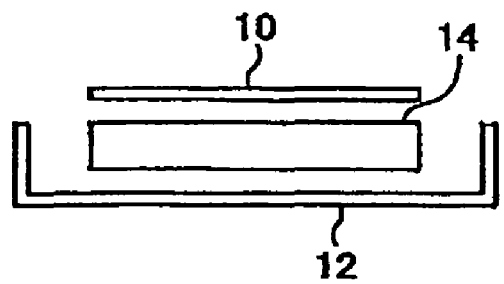
(B)
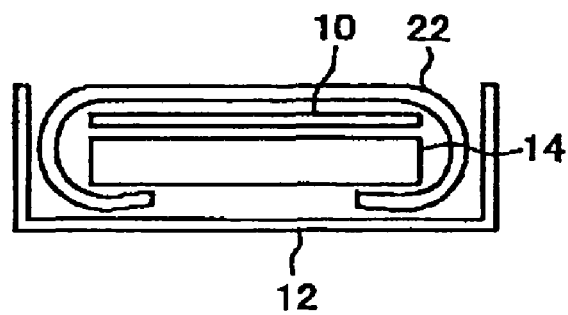
FIG. 14
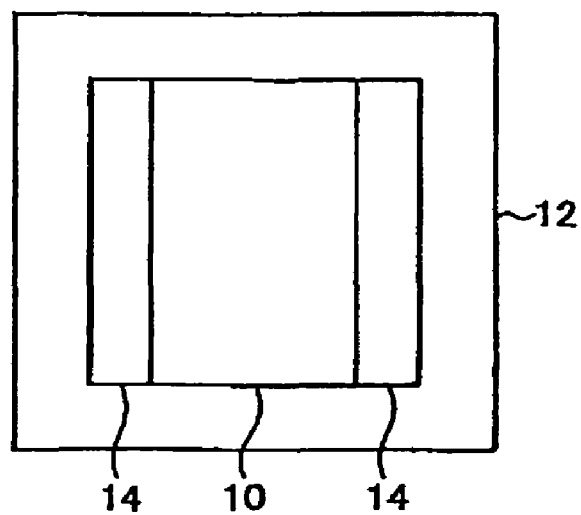

(C)

FIG. 16
(C)
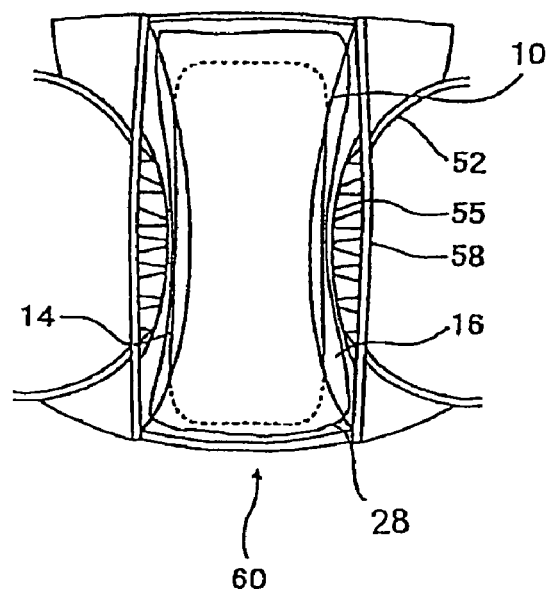
(D)
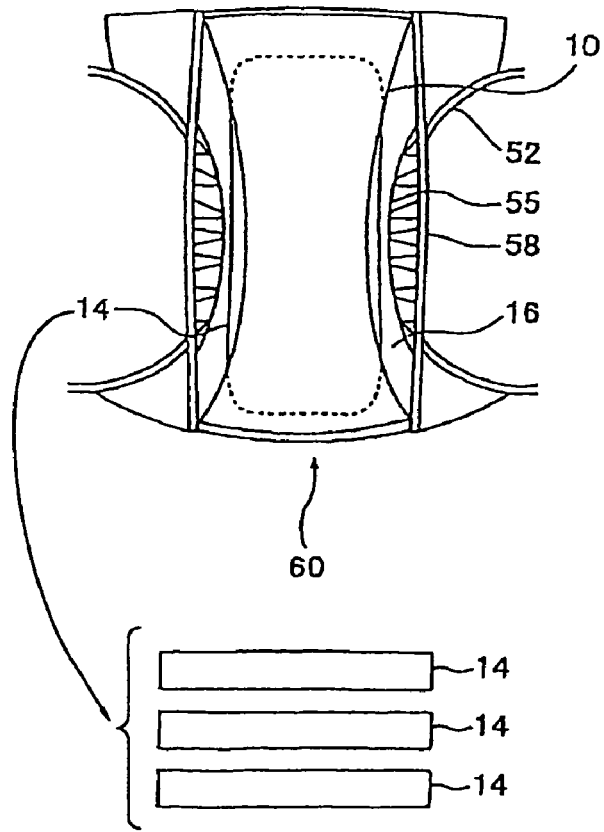

FIG. 18
(A)
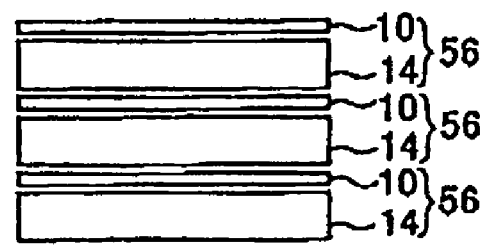
(B)
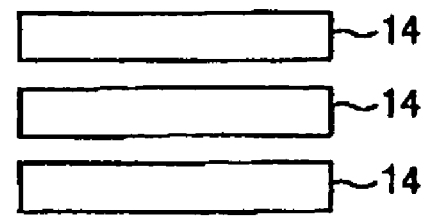
(C)
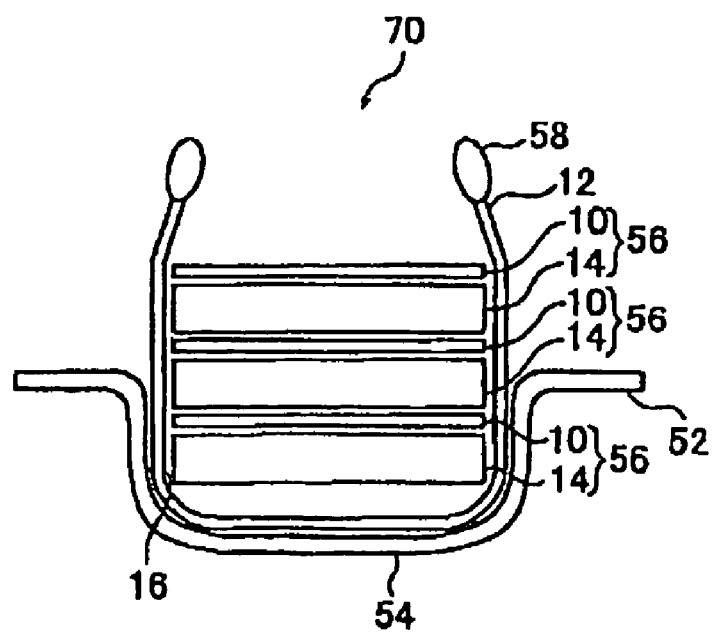

FIG.19
(A)
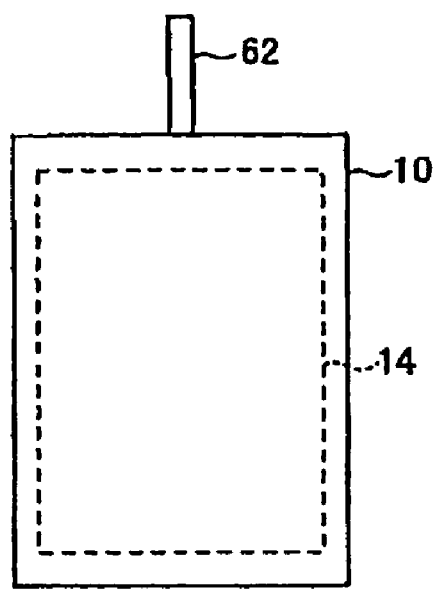
(B)
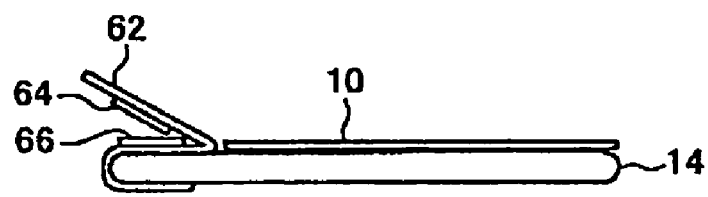
(C)
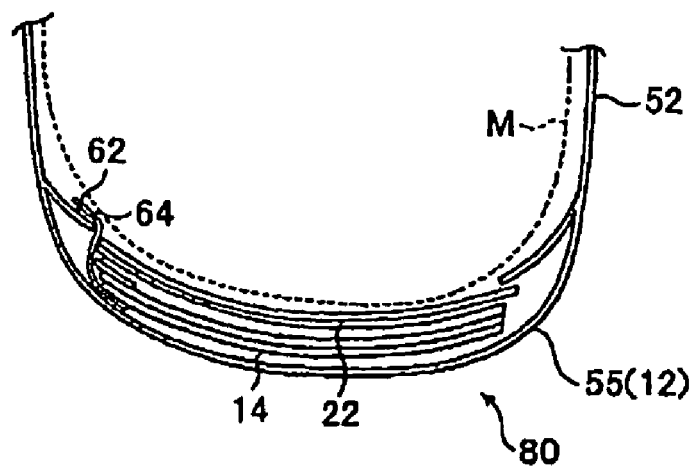

FIG. 24
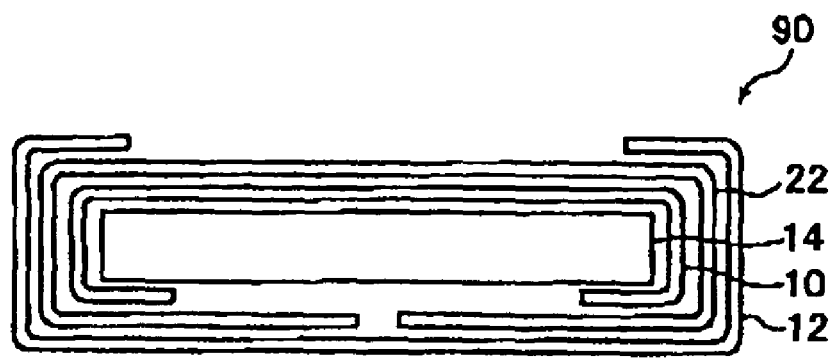
FIG. 25
(A)
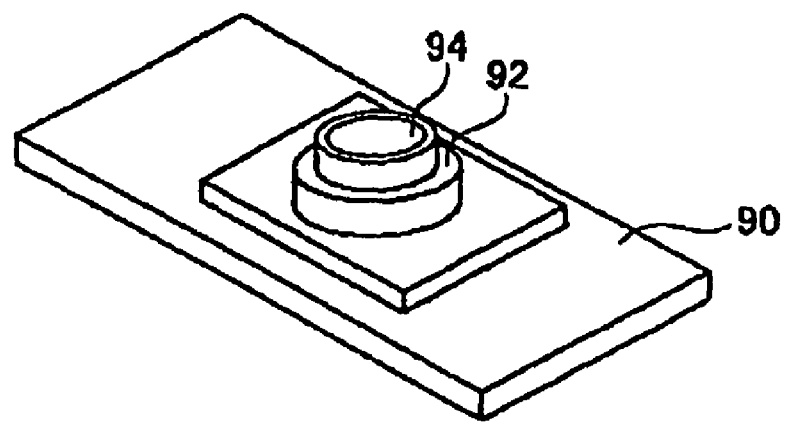
(B)
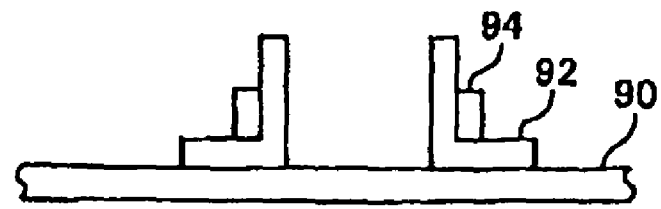

FIG. 26
(A)
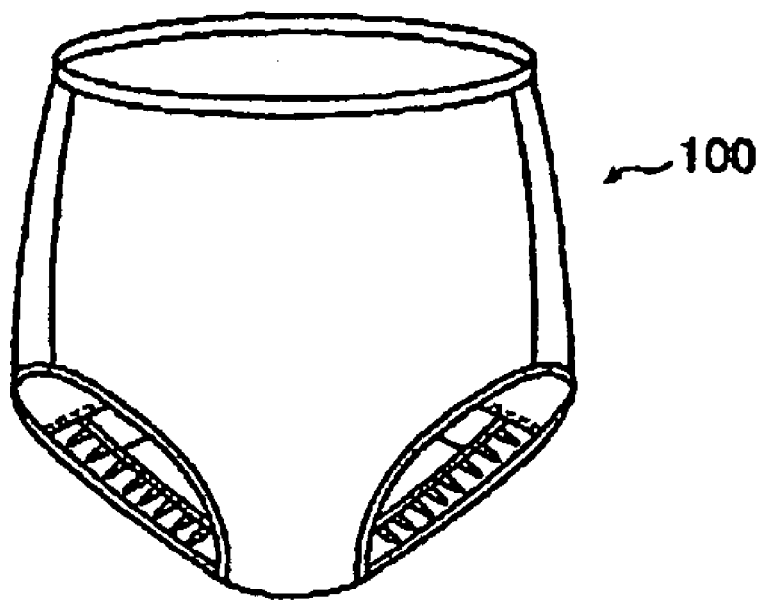
(B)
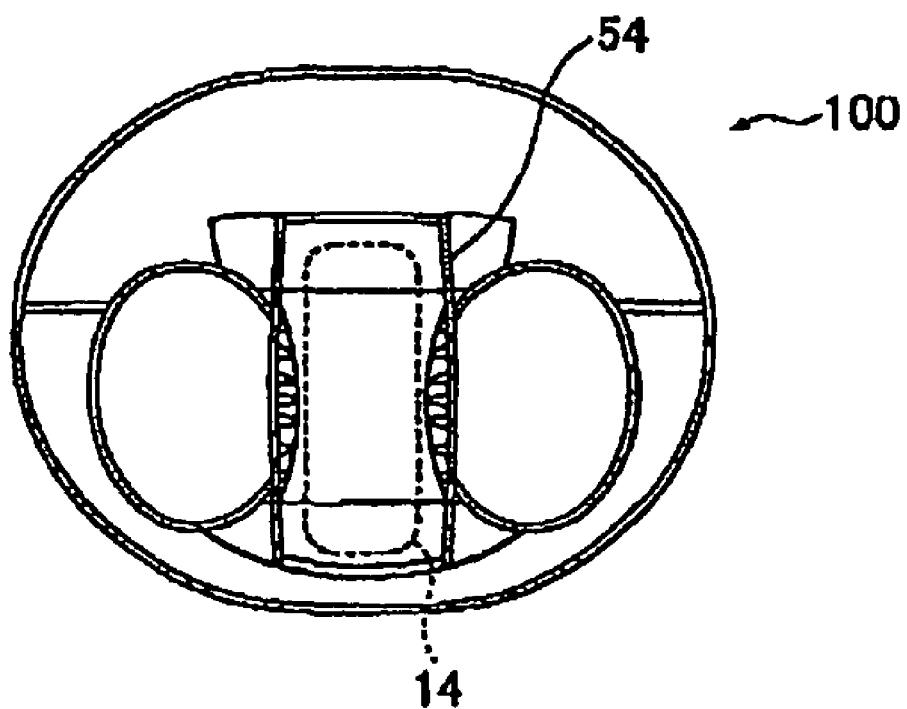

FIG. 27
(A)
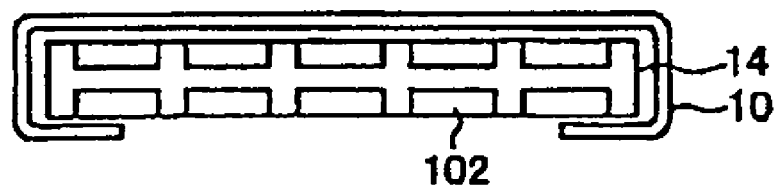
(B)
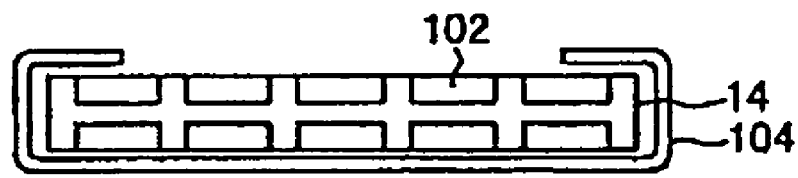
(C)
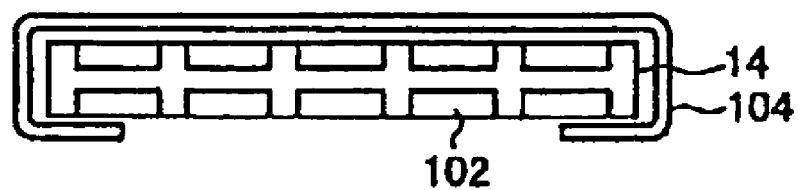

FIG. 28
(A)
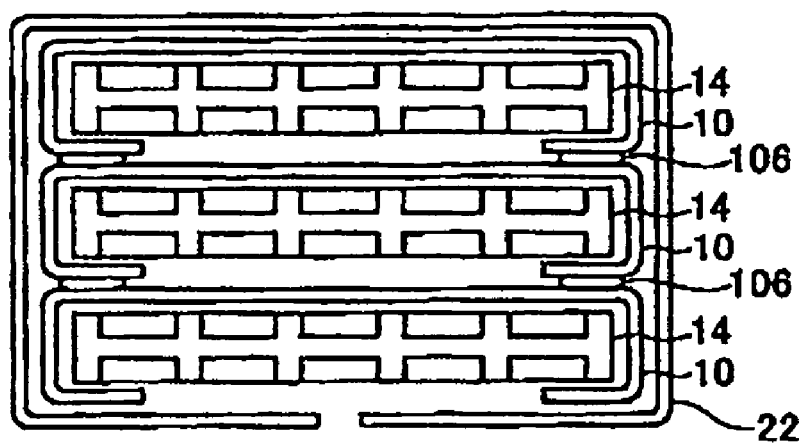
(B)
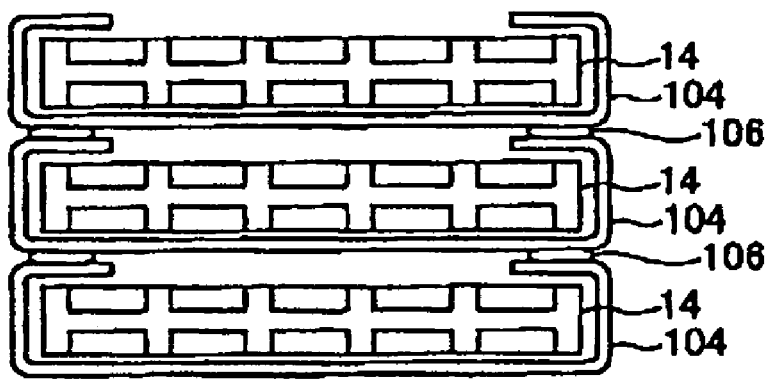
(C)
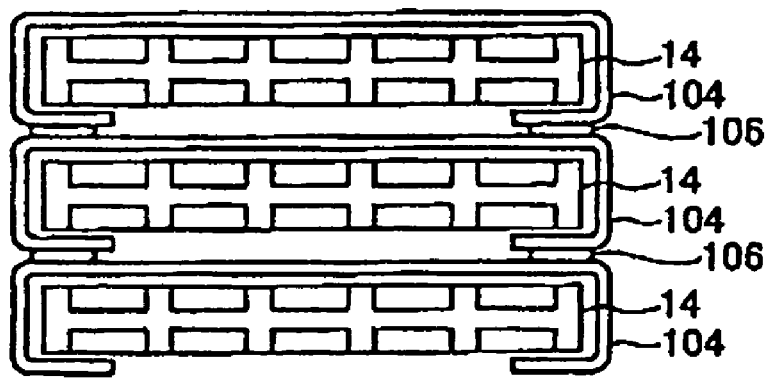

FIG. 29
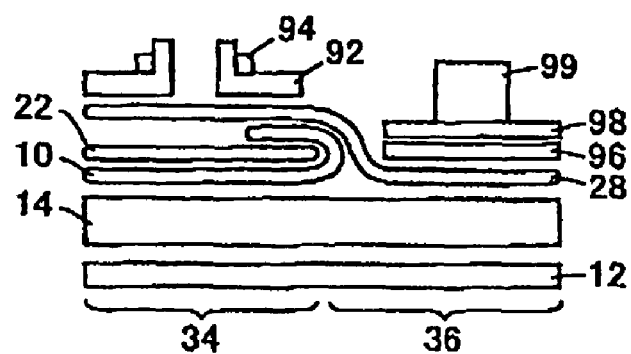
FIG. 30
(A) 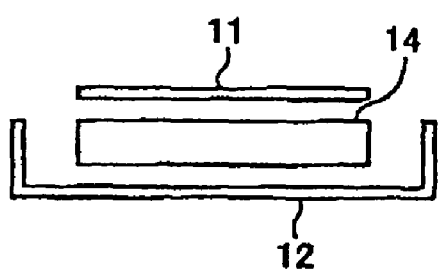
Prior Art
(B) 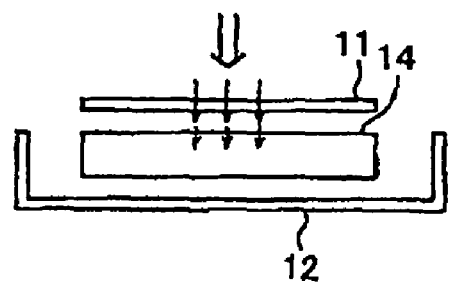
Prior Art

ABSORBENT PRODUCT WITH NONPERMEABLE SURFACE SHEET

BACKGROUND

1. Technical Field

The present disclosure relates to an absorbent product. More precisely, it relates to an absorbent product capable of preventing the absorbing rate of discharged liquid from significantly lowering with the elapse of time, and having a very small re-wet amount.

2. Background Art

Conventional absorbent products include a liquid-permeable top sheet positioned on the upper side (the side nearer to the wearer's body), a liquid-impermeable back sheet positioned on the lower side (the side away from the wearer's body), and an absorber positioned between these. In case discharged liquid such as urine, feces, and body fluid containing blood (hereinafter referred simply as "discharged liquid" or "liquid") is supplied to this absorbent product, the discharged liquid first passes through the liquid-permeable top sheet and reaches the absorber. In the absorber, the discharged liquid diffuses to the lower side, and when it reaches the liquid-impermeable back sheet, the diffusion ceases. All of the conventional absorbent products use a discharged liquid absorbing mechanism such as this.

However, the conventional absorbent products which use the aforementioned absorbing mechanism have two major intrinsic problems. The first problem is that the absorbing rate is lowered as the absorber's absorption volume of discharged liquid increases. The second problem is that the amount of liquid returning from the absorber to the top sheet, or the re-wet amount, increases as the absorption volume of discharged liquid grows larger, especially in the vicinity of the limit of absorbing capacity. These cause an increase of moisture percentage on the surface of the wearer's body during and after discharging of the liquid, making it uncomfortable to keep it on, and easily susceptible to becoming sweaty, as well as becoming a primary cause of diaper rash.

While on the other hand, in an effort to solve these problems, diverse suggestions regarding performance, structure, air-permeability, etc. of the top sheet and the absorber have been made, but so far no technique reaching the ultimate solution has been found.

SUMMARY

An object of the present disclosure, therefore, is to provide an absorbent product which is capable of preventing the absorbing rate from significantly lowering with the elapse of time from the start of use to a final stage when the absorbing capacity of the product reaches a limit, and has a very small re-wet amount.

As a result of research devoted to achieving the above objective, defying traditional common sense, it was discovered that it is possible, by positioning on the upper side of an absorber a liquid-impermeable surface sheet in place of a liquid-permeable top sheet to which the discharged liquid is supplied, and by designing a structure wherein a flow passage from the upper side of a surface sheet reaching the lower portion of an absorber is provided, to realize an absorbing mechanism that diffuses a part or all of the discharged liquid from the lower side to the upper side of an absorber. Furthermore, it was discovered that, by the above absorbing mechanism, the absorbing rate is prevented from significantly lowering with the elapse of time, and the re-wet amount becomes extremely small.

In other words, the absorbent product disclosed herein provides one or more of the following features:

(1) An absorbent product with a liquid-impermeable surface sheet positioned on the upper side, a liquid-impermeable back sheet positioned on the lower side, and an absorber containing super absorbent polymer to absorb discharged liquid positioned between the surface sheet and the back sheet, wherein a flow passage is provided to allow a part or all of the discharged liquid supplied to the surface sheet to a side of the back sheet of the absorber.

The flow passage being provided in at least one of the following portions of the absorber; on both front and back ends, on both right and left ends, and in the center.

The surface sheet being composed of a single-layer synthetic resin film.

The surface sheet being composed of a laminate of a synthetic resin film and a nonwoven fabric provided on a surface of the upper side of the synthetic resin film.

The synthetic resin film has concave and convex portions that constitute the flow passage.

The surface sheet being positioned in such a way that a portion of the surface of the upper side of the absorber is exposed.

The surface sheet containing a liquid-permeable portion.

A liquid-permeable guide sheet with the flow passage being laminated to at least a portion of the surface of the upper side of the surface sheet.

The guide sheet covering at least a portion of the lateral sides of the absorber directly or, over the surface sheet.

The guide sheet has concave and convex portions that constitute the flow passage and has apertures in some of or in all of the convex portions.

A skin-contact sheet composed of liquid-permeable nonwoven fabric being laminated to at least a portion of the surface of the upper side of either the surface sheet or the guide sheet.

The back sheet is composed of a synthetic resin film.

The synthetic resin film that constitutes the back sheet has air-permeability.

The back sheet being composed of a laminate of a synthetic resin film and a nonwoven fabric provided on the surface of the lower side of the synthetic resin film.

Both the synthetic resin film and the nonwoven fabric that constitute the back sheet have air-permeability.

The synthetic resin film that constitutes the back sheet has concave and convex portions and having apertures in some of or in all of the convex portions, and the nonwoven fabric that constitutes the back sheet being a water-resistant laminate, of two layers or more, containing one layer or more than one layer of a spunbond nonwoven fabric and one layer or more than one layer of meltblown nonwoven fabric.

The synthetic resin film that constitutes the back sheet has concave and convex portions constituting a liquid trap portion on the surface of the upper side thereof.

The absorber being composed of a mixture of super absorbent polymer and fluffy pulp wrapped with a liquid-permeable core-wrapping sheet.

The absorber has two layers of liquid-permeable nonwoven fabrics and super absorbent polymer inserted in-between.

The absorber being constructed by having super absorbent polymer supported by means of coating on a liquid-permeable nonwoven fabric.

A content of the super absorbent polymer in the absorber being 50 wt % or more.

The product being an absorbent product main body that can form an internal space to contain a wearer's objective region when worn;

housing for an absorber unit adjacent to the absorbent product main body, continued to the internal space, and containing the back sheet on an inner wall thereof; and an absorber unit structured by combining at least the surface sheet and the absorber, being received removably by the housing for the absorber unit are provided.

The guide sheet being included at least in a portion between the absorbent product main body and the housing for the absorber unit.

A liquid-permeable skin-contact sheet being included at least in a portion between the absorbent product main body and the housing for the absorber unit.

The product has laminated plural number of the absorber units being included in the housing for the absorber unit.

The product has an absorbent product main body that can form an internal space to contain a wearer's objective region when worn; housing for an absorber adjacent to the absorbent product main body, continued to the internal space, and containing the back sheet on an inner wall thereof, and an absorber received removably by the housing for the absorber are provided; and, furthermore, the surface sheet is included at least in a portion between the absorbent product main body and the housing for the absorber.

The guide sheet is laminated on the surface of the upper side of the surface sheet.

A liquid-permeable skin-contact sheet is provided at least on a portion of the surface of the upper side of the surface sheet or the guide sheet.

Laminated plural number of absorbers are included in the housing for the absorber.

A urine-disposing portion extending from the center to the front section and a feces-disposing portion extending from the center to the back section are provided and the surface sheet is provided only at the urine-disposing portion.

A liquid-impermeable or water-resistant back-flow preventing sheet is included inside and/or on the upper side of the absorber, at least at the feces-disposing portion.

A re-wet amount measured under a load of 0.1 psi, 5 minutes after the beginning of the absorption to allow a sodium chloride solution of 0.9 wt % in the amount equivalent to 50% of the absorbing capacity of the absorber to be absorbed in the absorber at 25% under no load, is 5 mL or less.

The re-wet amount is 2 mL or less.

The absorber's absorbing capacity of sodium chloride solution of 0.9 wt % is 300 mL or more, and when saline is added to be absorbed by the absorber in the amount of 100 mL each time in three separate additions under no load in every 10 minutes, an average re-wet amount after three additions is 5 mL or less, and the standard deviation of the re-wet amount is 3 mL or less; and when saline is added to be absorbed by the absorber in the amount of 100 mL each time in three separate additions under a load of 0.1 psi in every 10 minutes, the mean absorption time of the three additions is 30 seconds or less, and the standard deviation of the absorption time is 2 seconds or less.

BRIEF DESCRIPTION OF THE DRAWINGS

FIGS. 1(A) and (B) are a set of illustrative cross-section views showing a portion of an example of the absorbent product;

FIGS. 2(A)-(D) are a group of illustrative top views and cross-section views showing a portion of examples of the absorbent product of the present disclosure;

FIG. 3 (A) is an illustrative perspective view of an example of the surface sheet with a large number of projections and FIG. 3 (B) is its illustrative cross-section view;

FIGS. 4 (A) and (B) are illustrative cross-section views, each showing an example of the surface sheet with V-shape grooves, and FIGS. 4 (C) and (D) are illustrative cross-section views each showing an example of the ribbed surface sheet;

FIGS. 5 (A) and (B) are illustrative perspective views, each showing an example of the surface sheet with V-shape grooves;

FIG. 9 is a group of illustrative views, cross-sectional (FIGS. 9 (A) through (D)) and perspective (FIG. 9 (E)), showing a portion of examples of the absorbent product;

FIGS. 11(A)-(B) are a set of illustrative top views, each showing a portion of examples of the absorbent product;

FIGS. 12(A)-(B) are a set of illustrative top views, showing examples of the back sheet used;

FIGS. 13(A)-(B) are a set of illustrative cross-section views, each showing a portion of examples of the absorbent product;

FIG. 14 is an illustrative top view showing a portion of an example of the absorbent product;

FIGS. 16(A)-(D) are a group of illustrative top views showing a portion of an example of the absorbent product;

FIG. 18 (A) is an illustrative cross-section view showing an example of laminated plural pieces of absorber units. FIG. 18 (B) is an illustrative cross-section view showing an example of laminated plural pieces of absorbers, and FIG. 18 (C) is an illustrative cross-section view showing an example of a portion of the absorbent product of the present disclosure, including laminated plural pieces of absorber units;

FIGS. 19(A)-(C) are a group of explanatory drawings, each showing an example of the absorbent product of the present disclosure with a member for pulling out;

FIG. 24 is an illustrative cross-section view of the absorbent product used in the Examples;

FIGS. 25(A)-(B) are a set of explanatory drawings showing the method of measuring absorbing rate in the Examples;

FIGS. 26(A)-(B) are an illustrative front view and an illustrative top view showing the absorbent product that includes plural pieces of absorber units and is used in the Examples;

FIGS. 27(A)-(C) are a set of illustrative cross-section views of the absorber units used in the Examples;

FIGS. 28(A)-(C) are a set of illustrative cross-section views of the absorbent products using the absorber units shown in FIG. 27;

FIG. 29 is an explanatory drawing showing the method of measuring the re-wet amount of the absorbent products, for both urine- and feces-disposing, used in the Examples; and FIGS. 30(A)-(B) are a set of illustrative cross-section views showing a portion of an example of a conventional absorbent product.

DETAILED DESCRIPTION OF EMBODIMENTS

Figure 6:
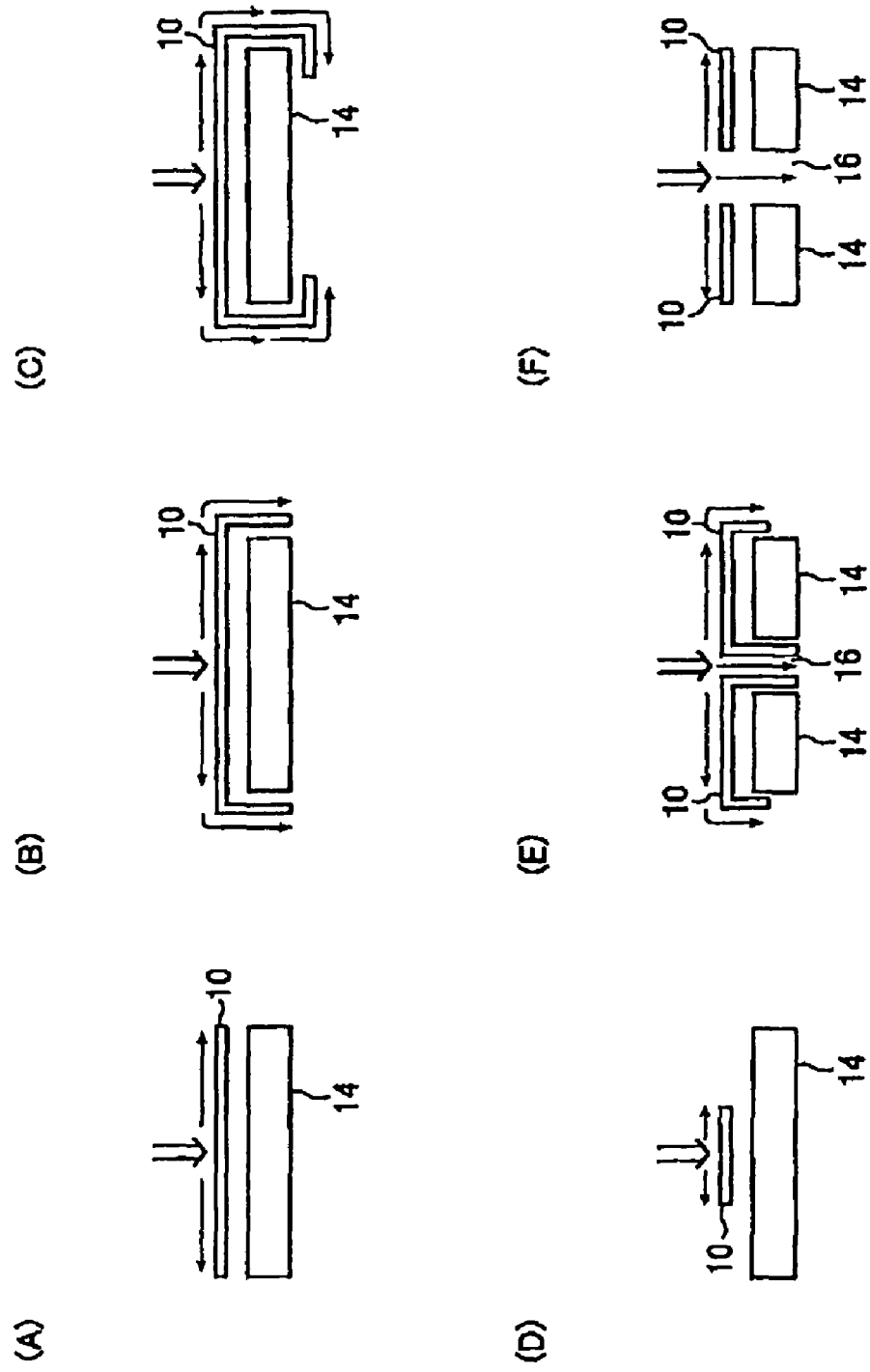
FIGS. 6(A)-(F) are a group of illustrative cross-section views, each showing a portion of examples of the absorbent product.

Hereinafter, the absorbent products of the present disclosure will be described in detail in accordance with preferred embodiments shown in accompanying drawings. Note that each drawing used to describe the present disclosure is an illustrative drawing and is exaggerated in the thickness of the absorbent product.

FIGS. 1(A) and (B) are a set of illustrative cross-section views showing a portion of an example of the absorbent according to this disclosure. FIGS. 1(A) and (B), the direction perpendicular to the surface of the page is the anteroposterior direction of the absorbent product (in other words, the direction equivalent to front to back of the wearer's body when it is worn) (hereinafter the same applies to all cross-section views). FIG. 1 (A) is an explanatory drawing of a structure of the absorbent product and FIG. 1 (B) is an explanatory drawing of the absorbent product use.

As shown in FIG. 1 (A), the absorbent product of the present disclosure includes a liquid-impermeable surface sheet 10, a liquid-impermeable back sheet 12, and an absorber 14 containing super absorbent polymer (hereinafter also referred to as "SAP"), so that discharged liquid can be absorbed and positioned between the surface sheet 10 and the back sheet 12.

When discharged liquid is supplied to the absorbent product, as shown in FIG. 1 (B), because the surface sheet 10 positioned on the upper side is liquid-impermeable, the discharged liquid moves on the surface of the surface sheet 10 to the end portions of it. The discharged liquid that has moved to the end portions of the surface sheet 10, because the back sheet 12 is liquid-impermeable, moves along the inner surface of the back sheet 12 in the flow passage 16 formed between the absorber 14 and the back sheet 12, while a part of it is being absorbed by the absorber 14, mainly into the bottom side of the absorber 14. In this way, the discharged liquid is absorbed by the bottom side of the absorber 14, and then is diffused to the upper side.

As described above, the absorbent product of the present disclosure is characterized by comprising a flow passage to allow a part or all of the discharged liquid supplied to the surface sheet to move to the back sheet side. It is preferred that this flow passage is provided in at least one of the following portions of the absorber; both front and back ends, both right and left ends, and the center.

FIGS. 2(A)-(D) are a group of illustrative top views (FIGS. 2 (A) and (B)) and cross-section views (FIGS. 2 (C) and (D)) showing a portion of examples of the absorbent product of the present disclosure. In FIGS. 2 (A) and (B), the top-to-bottom direction of the page represents the front-to-back direction of the absorbent product (hereinafter the same applies to all top views). In FIG. 2, as a matter of explanatory convenience, only the surface sheet 10, back sheet 12, and the absorber 14 are shown.

In the absorbent product shown in FIGS. 2 (A) and (C), the surface sheet 10 fully covers the upper surface of the absorber 14, and the lateral faces and the lower surface thereof are fully covered with the back sheet 12. This absorbent product has the flow passages in all of the following portions of the absorber 14: the front end portion A, back end portion B, left end portion C, and the right end portion D.

In the absorbent product shown in FIGS. 2 (B) and (D), two absorbers 14 are positioned side by side with a space in between. Each of two surface sheets 10 fully covers respectively the upper surface of each of the two absorbers 14, and the outer lateral faces and the lower surface thereof are fully covered with one sheet of the back sheet 12. This absorbent product has the flow passages in all of the following portions of the absorber 14: the front end portion A, back end portion B, left end portion C, right end portion D, and the center portion E.

FIG. 30 is a set of illustrative cross-section views showing a portion of an example of a conventional absorbent product. FIG. 30 (A) is an explanatory drawing showing the structure of a conventional absorbent product and FIG. 30 (B) is an explanatory drawing of a conventional absorber in use.

A conventional absorbent product typically includes a liquid-permeable top sheet 11, a liquid-impermeable back sheet 12, and an absorber 14 positioned between the top sheet 11 and the back sheet 12.

When discharged liquid is supplied to a conventional absorbent product, as shown in FIG. 30 (B), because the top sheet 11 positioned on the upper side is liquid-permeable, the discharged liquid passes through the top sheet 11, is absorbed by the absorber from the top side thereof, and then is diffused to the lower side.

In contrast to this, the absorbent product of the present disclosure is characterized by realizing an absorbing mechanism that diffuses a part of or all of the discharged liquid from the lower side to the upper side of the absorber 14 by the structure described above. This mechanism prevents the absorbing rate from significantly lowering with the elapse of time, and ensures a very small re-wet amount.

The surface sheet 10 used in the present disclosure is liquid-impermeable. In this specification, "liquid-impermeable" represents a property of not in effect allowing the discharged liquid to permeate.

There is no limit in particular to the material or the structure of the surface sheet 10, as long as it is liquid-impermeable. For example, a single-layer synthetic resin film, and a laminate of a synthetic resin film and a nonwoven fabric provided on the surface of the upper side of the synthetic resin film, are preferred. As the synthetic resin film, a film made of resin such as PE (polyethylene), PP (polypropylene), PET (polyethylene terephthalate), polyurethane, or cross-linked PVA (polyvinyl alcohol) and an air-permeable but not liquid-permeable, in other words, breathable film made of above-described resins can be typically employed.

One of the preferred embodiments of the synthetic resin film used for a surface sheet 10 is the type with concave and convex portions constituting flow passages 16. However, when the absorbent product has a guide sheet as hereinafter described, even if the synthetic resin film does not have concave and convex portions to form flow passages 16, it will also be suitable for use.

Furthermore, where flat, smooth and relatively soft synthetic resin film is used as a surface sheet 10, if the surface of the absorber on which the surface sheet is positioned has concave and convex portions, the film may be deformed to be concave and convex, resulting in retention of the discharged liquid. In this case, however, the discharged liquid can be quickly moved by pressure-bonding the synthetic resin film and the upper surface of the absorber to smooth them out, or by designing a roof-like structure with a raised center portion and the slopes on both sides thereof.

As the configuration with concave and convex portions, the following can be exemplified: a configuration with a large number of projections, a configuration with grooves such as V-shaped or U-shaped grooves, an imbricate configuration (as imbricate scales), and a ribbed configuration.

FIG. 3 (A) is an illustrative perspective view of an example of the surface sheet with a large number of projections and FIG. 3 (B) is its illustrative cross-section view.

On the surface sheet 10a, a continuous series of a large number of concave portions function as flow passages 16 for the discharged liquid. The surface sheet 10a shown in FIG. 3 has a large number of projections 18 forming convex portions.

As for the size of the concave and convex portions of the surface sheet 10a, when taking into account its handling, cost, etc., it is preferred that the projections 18 forming the convex portions are 0.3 mm or greater in height, more preferably 0.5 to 1.5 mm.

The surface sheet 10a has the advantage of not inhibiting the flow of discharged liquid, even if the convex portions are somewhat deformed when in use.

FIGS. 4 (A) and (B) are illustrative cross-section views, each showing an example of the surface sheet with V-shape grooves respectively, and FIGS. 4 (C) and (D) are illustrative cross-section views, each showing an example of the ribbed surface sheet.

FIGS. 5 (A) and (B) are illustrative perspective views, each showing an example of the surface sheet with V-shape grooves. In FIG. 5 (A), V-shape grooves are formed in one direction only, while in FIG. 5 (B) V-shape grooves are formed in two mutually perpendicular directions. Note that there is no limit in particular to the shape, direction, number, intervals, etc. of the grooves. The same applies to the ribs.

The positional relationship of the surface sheet 10 and the absorber 14 is explained below.

As described above, the surface sheet 10 is positioned on the upper side of the absorber 14. More precisely, examples include, but are not limited to, positional relationships described below.

FIG. 6 is a group of illustrative cross-section views, each showing a portion of examples of the absorbent product. In FIG. 6, as a matter of explanatory convenience, only the surface sheet 10 and the absorber 14 are shown.

In FIG. 6 (A), the surface sheet 10 fully covers, in the left-to-right direction, the upper surface of the absorber 14. In this case, the discharged liquid supplied to the surface sheet 10 moves quickly along the surface of the surface sheet 10 to the upper portion of the right and left ends of the absorber 14.

In FIG. 6 (B), the surface sheet 10 fully covers, in the left-to-right direction, the upper surface of the absorber 14, and further covers the right and left lateral surfaces thereof. In this case, the discharged liquid supplied to the surface sheet 10 moves quickly along the surface of the surface sheet 10 to the lower portion of the right and left ends of the absorber 14. Therefore, the proportion of discharged liquid absorbed from the lower portion of the absorber 14 is greater in comparison to the case described in FIG. 6 (A).

In FIG. 6 (C), the surface sheet 10 fully covers, in the left-to-right direction, the upper surface of the absorber 14, and further covers the right and left lateral surfaces, as well as a portion of the lower surface thereof. In this case, the discharged liquid supplied to the surface sheet 10 moves quickly along the surface of the surface sheet 10 to the lower surface of the absorber 14. Therefore, the discharged liquid is more easily absorbed from the center portion of the lower surface of the absorber 14 than in the case shown in FIG. 6 (B).

In FIG. 6 (D), the surface sheet 10 partially covers, in the left-to-right direction, the upper surface of the absorber 14. In this case, the discharged liquid supplied to the surface sheet 10 moves quickly along the surface of the surface sheet 10 to the upper surface nearer to the ends of the absorber 14. A part of the discharged liquid, therefore, is absorbed from the upper surface of the absorber 14, but the rest is absorbed from the lateral surfaces and the lower surface of the absorber 14. As described above, a part of the discharged liquid may be absorbed from other portions of the absorber 14 than the lower surface thereof.

In FIG. 6 (E), two absorbers 14 are positioned side by side, with the flow passage 16 in between, and each of two surface sheets 10 fully covers, in the left-to-right direction, the upper surface of each of the two absorbers 14, as well as the lateral surfaces on right and left thereof. Furthermore, the surface sheet 10 extends into the flow passage 16. In this case, the discharged liquid supplied to the surface sheet 10 moves quickly along the surface of the surface sheet 10 to the lower portion of the flow passage 16 while a part of the liquid moves to the lower portion of the outside ends also. The discharged liquid, therefore, is easily absorbed from the portions of the absorber equivalent to the center portion as well as the outside portions on both sides of the absorbent product.

In FIG. 6 (F), two absorbers 14 are positioned side by side with the flow passage 16 in between, and each of two surface sheets 10 fully covers the upper surface of each of the two absorbers 14. In this case, the discharged liquid supplied to the surface sheet 10 moves quickly along the surface of the surface sheet 10 to the upper portion of the outside end of each absorber 14, while it also moves through the flow passage 16 to the lower portion of the flow passage 16. The discharged liquid is easily absorbed from the lateral surfaces as well as the lower surface of each absorber 14.

Figure 7:
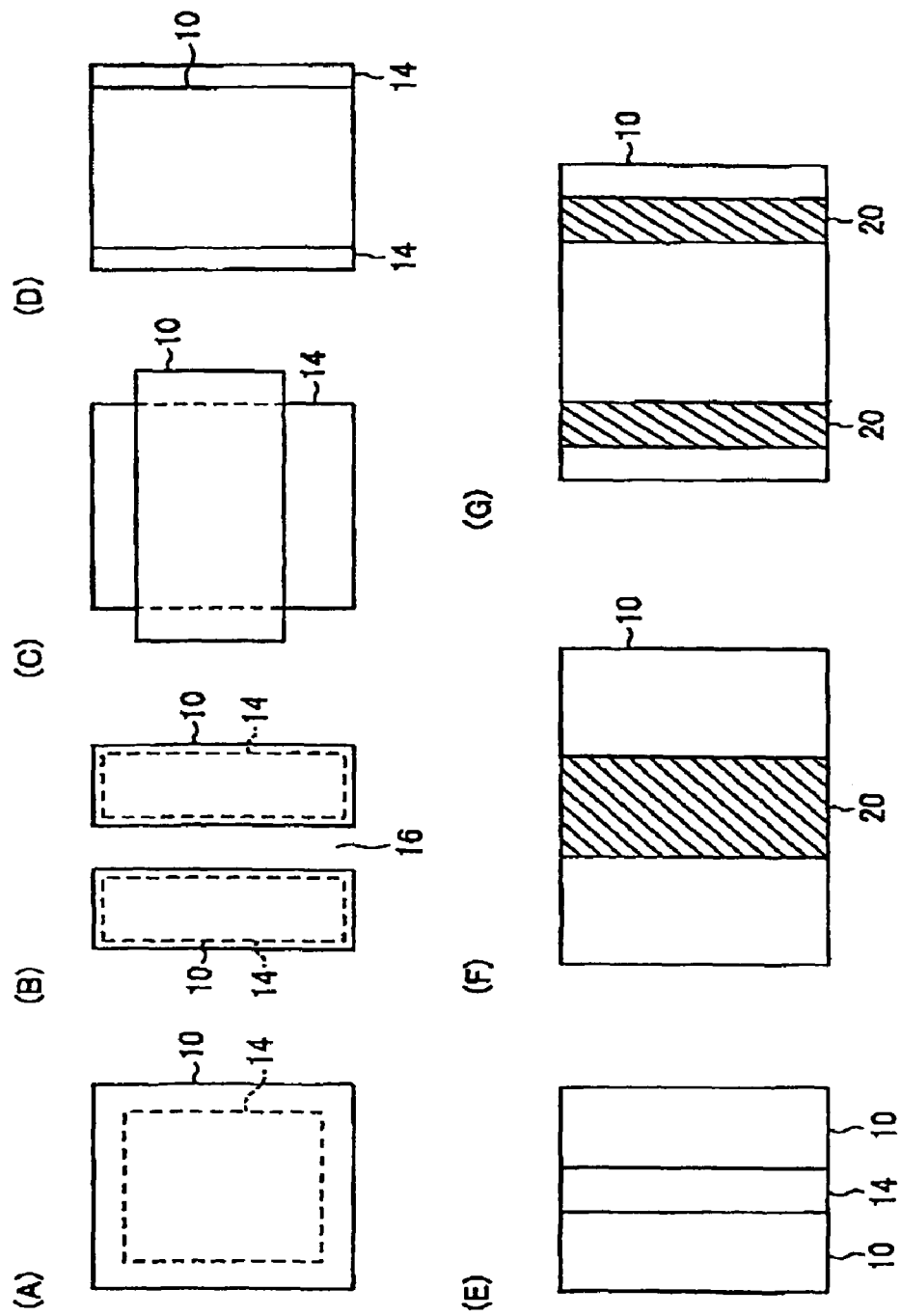
FIGS. 7(A)-(G) are a group of illustrative top views, each showing a portion of examples of the absorbent product.

FIG. 7 is a group of illustrative top views, each showing a portion of examples of the absorbent product. In FIG. 7, as a matter of explanatory convenience, only the surface sheet 10 and the absorber 14 are shown.

In FIG. 7 (A), the surface sheet 10 fully covers the upper surface of the absorber 14.

In FIG. 7 (B), two absorbers 14 are positioned side by side with the flow passage 16 in between, and each of two surface sheets 10 fully covers the upper surface of each of the two absorbers 14.

In FIG. 7 (C), the surface sheet 10 fully covers, in the left-to-right direction, a portion, in the anteroposterior direction, of the upper surface of the absorber 14. A portion of the upper surface of the absorber 14 is exposed in the front and back end portions of the surface sheet 10.

In FIG. 7 (D), the surface sheet 10 fully covers, in the anteroposterior direction, a portion, in the left-to-right direction, of the upper surface of the absorber 14. The upper surface of the absorber 14 is partially exposed in the right and left end portions of the surface sheet 10.

In FIG. 7 (E), two surface sheets 10 cover the right and left end portions of the upper surface of the absorber 14, and a portion of the upper surface of the absorber is exposed in the center portion.

In FIG. 7 (F), the surface sheet 10 fully covers the upper surface of the absorber 14, but the surface sheet 10 has a liquid-permeable portion 20 in the center in the left-to-right direction.

In FIG. 7 (G), the surface sheet 10 fully covers the upper surface of the absorber 14, but the surface sheet 10 has liquid-permeable portions 20 at two predetermined portions in the left-to-right direction.

There is no limit in particular to the material, structure, etc. of the liquid-permeable portions 20 in FIGS. 7 (F) and (G) as long as they are liquid-permeable. For example, the surface sheet 10 with apertures to make it liquid-permeable is acceptable, a portion of the surface sheet 10 may be constructed with a liquid-permeable material (for example, a spunbond nonwoven fabric), etc. In this specification, "liquid-permeable" represents a characteristic of in effect allowing the discharged liquid to permeate.

In both cases of FIGS. 7 (A) and (B), the discharged liquid supplied to the surface sheet 10 is absorbed from the lateral and lower surfaces of the absorber 14 without being absorbed by the upper surface thereof.

In all of the cases of FIGS. 7 (C) through (G), a part of the discharged liquid supplied to the surface sheet 10 is absorbed from the upper surface of the absorber 14 through the exposed portions of the absorber 14 or through the liquid-permeable portions 20, and the rest is absorbed from the lateral surfaces and lower surface of the absorber 14.

As just described, the embodiments in which the discharged liquid is absorbed from all portions including the upper, lateral, and lower surfaces of the absorber 14 are preferred in terms of increased absorption rate, but in terms of the re-wet amount, the performance tends to get slightly worse. Another embodiment of the absorbent product is to have the surface sheet positioned so as to expose a portion of the upper surface of the absorber, an embodiment wherein the surface sheet is positioned only partially in the vicinity of the urinary excretion part of the wearer to ensure dryness of that local part.

The positional relationships described in FIGS. 6 (A) through (F) and the positional relationships described in FIGS. 7 (A) through (G) may be combined in as many ways as possible, to realize various positional arrangements. Furthermore, the surface sheet 10 and the absorber 14 may also be arranged in other positional relationships than those described above.

One of the preferred embodiments has a liquid-permeable guide sheet with the flow passage laminated to at least a portion of the surface of the upper side of the surface sheet. The guide sheet assists the supplied discharged liquid to move to the lower side of the absorber through its flow passage. In case the guide sheet is laminated, therefore, even if the synthetic resin film constituting the surface sheet does not have concave and convex portions to form flow passages, rapid diffusion, by the guide sheet, of the discharged liquid to the lower side of the absorber will be accomplished.

The discharged liquid moves through the flow passages of the guide sheet by capillary action, moistening, penetration, and diffusion. In order to ensure efficient movement of the discharged liquid, it is preferred that the guide sheet has hydrophilicity and a certain extent of thickness. More precisely, for example, a film with concave-convex apertures having liquid distribution effect or a concave-convex molded plastic net with liquid distribution effect (suggested in the pamphlet of International Publication No. 02/065965, for example); and bulky laminated nonwoven fabrics (for example, a composite sheet made by bonding a paper or nonwoven fabric layer having a flat and smooth surface and a fiber web layer having a bulky surface of concave and convex portions suggested in the specification of JP 2001-297161 A and the specification of JP 2001-297162 A) may be used.

One of the preferred embodiments of the guide sheet has concave and convex portions constituting the flow passages and has apertures in part of or all of the convex portions.

Figure 8:
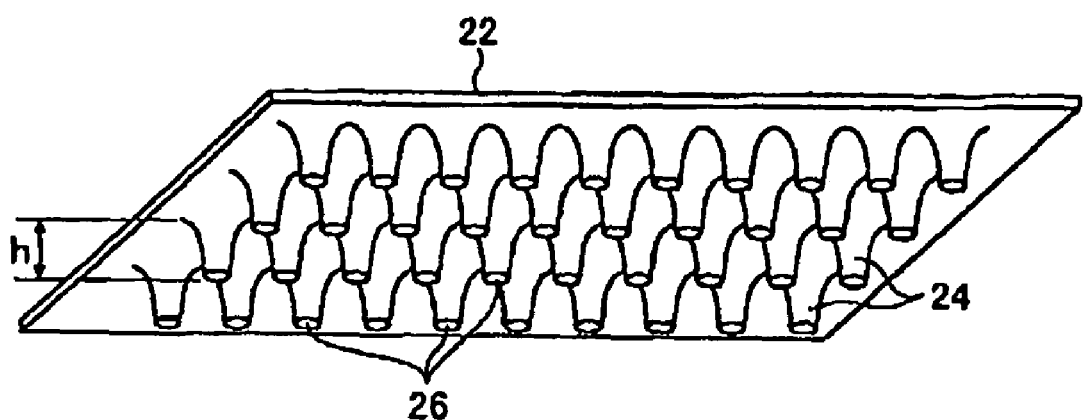
FIG. 8 is an illustrative perspective view showing an example of the guide sheet that has concave and convex portions constituting flow passages wherein every convex portion has an aperture.

FIG. 8 is an illustrative perspective view showing an example of the guide sheet that has concave and convex portions constituting flow passages, wherein every convex portion has an aperture.

On the guide sheet 22, a continuous series of a large number of concave portions function as flow passages 16 for the discharged liquid. The guide sheet 22 shown in FIG. 8 has a large number of projections 24 forming convex portions, each projection 24 having an aperture 26 at the top.

In the case of a guide sheet with apertures at convex portions as shown in FIG. 8, even if it is made of hydrophobic material, these apertures will also function as the flow passages for the discharged liquid. In other words, the discharged liquid moves via the apertures from one side to the other side of the guide sheet.

The apertures may be provided only in some of the convex portions or in all of the convex portions. Furthermore, though there is no limit in particular to the number of apertures per unit area, 1.0 to 100 apertures/cm$^2$ is preferable.

As for the size of the concave and convex portions of the guide sheet 22, when taking into account its handling, cost, etc., it is preferred that the projections 24 forming the convex portions have a height h of 0.3 mm or greater, more preferably 0.5 to 1.5 mm.

The guide sheet 22 has an advantage of not inhibiting the flow of discharged liquid, even if the convex portions are somewhat deformed when in use.

It is preferred that the projections of the guide sheet 22 face downward. In this way, the flow passages formed in between the projections 24 and the surface of the surface sheet become large, resulting in smoother movement of the discharged liquid from the surface of the guide sheet to the surface of the surface sheet.

One of the preferred embodiments has a skin-contact sheet made of liquid-permeable nonwoven fabric laminated to at least a part of the surface of the upper side of the surface sheet or the guide sheet. The skin-contact sheet is a portion that directly touches the wearer's skin, and by providing this skin-contact sheet, the comfortability of the wearer may be improved. For the skin-contact sheet, the material used as a top sheet in the conventional absorbent products may be used, and skin-care performance, such as an antibacterial property, may be given to it. Furthermore, a special contact sheet such as the one suggested in the pamphlet of International Publication No. 02/00154 may also be used.

The preferred examples of the structure of the aforementioned surface sheet, guide sheet, and the skin-contact sheet will be explained in detail.

FIG. 9 is a group of illustrative views, cross-sectional (FIGS. 9 (A) through (D)) and perspective (FIG. 9 (E)), showing a portion of examples of the absorbent product. In FIG. 9, as a matter of explanatory convenience, only the surface sheet 10, absorber 14, guide sheet 22, and the skin-contact sheet 28 are shown.

In FIG. 9 (A), the surface sheet 10 is composed of a laminate of a synthetic resin film and a nonwoven fabric provided on the surface of the upper side of the synthetic resin film.

In FIG. 9 (B), the surface sheet 10 is composed of a single-layer synthetic resin film, wherein the synthetic resin film has concave and convex portions that form flow passages 16, and the skin-contact sheet 28 made of liquid-permeable nonwoven fabric is laminated on the surface of the upper side of the surface sheet 10.

In FIG. 9 (C), the surface sheet 10 is composed of a single-layer synthetic resin film, and the liquid-permeable guide sheet 22 with the flow passages 16 is laminated on the surface of the upper side of the surface sheet 10.

In FIG. 9 (D), the skin-contact sheet 28 made of liquid-permeable nonwoven fabric is further laminated on the surface of the upper side of the guide sheet shown in FIG. 9 (C).

In FIG. 9 (E), the surface sheet 10 is composed of a single-layer synthetic resin film, and the liquid-permeable guide sheet 22 with a large number of apertures 26 and the flow passages 16, is laminated on the surface of the upper side of the surface sheet 10. The surface sheet 10 and the guide sheet 22 are integrated by the bonding portions 22a.

Figure 10:
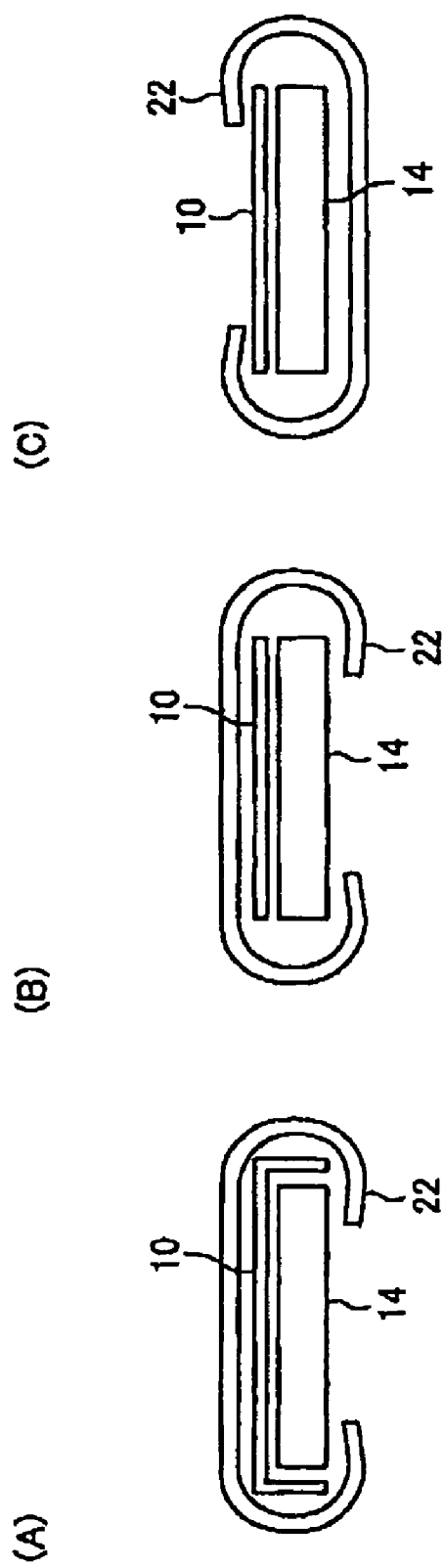
FIGS. 10(A)-(C) are a group of illustrative cross-section views, each showing a portion of examples of the absorbent product.

FIG. 10 is a group of illustrative cross-section views, each showing a portion of examples of the absorbent product. In FIG. 10, as a matter of explanatory convenience, only the surface sheet 10, absorber 14, and the guide sheet 22 are shown.

In FIG. 10 (A), the surface sheet 10 covers the upper surface as well as the left end and the right end portions of the absorber 14, and the guide sheet 22 covers the upper surface as well as the left end and the right end portions of the absorber 14, and further, a part of the lower surface thereof.

In FIG. 10 (B), the surface sheet 10 covers the upper surface of the absorber 14, and the guide sheet 22 covers the upper surface as well as the left and right end portions of the absorber 14.

In FIG. 10 (C), the surface sheet 10 covers the upper surface of the absorber 14, and the guide sheet 22 covers the lower surface as well as the left and right end portions of the absorber 14, and further, a part of the upper surface thereof.

As shown in FIGS. 10 (A) through (C), when the guide sheet 22 covers at least a part of the lateral surface of the absorber 14 directly or over the surface sheet 10, diffusion of the discharged liquid becomes faster.

FIG. 11 is a set of illustrative top views, each showing a portion of examples of the absorbent product. In FIG. 11, as a matter of explanatory convenience, only the surface sheet 10, absorber 14, and the guide sheet 22 are shown.

In FIG. 11 (A), the surface sheet 10 fully covers, in the anteroposterior direction, a portion in the left-to-right direction of the upper surface of the absorber 14. A portion of the upper surface of the absorber 14 is exposed in the right and left end portions of the surface sheet 10. And the guide sheet 22 fully covers in the left-to-right direction a portion, in the anteroposterior direction, of the upper surface of the surface sheet 10, and a portion of the upper surface of the absorber 14 and a portion of the upper surface of the surface sheet 10 are exposed.

In FIG. 11 (B), the surface sheet 10 and the absorber 14 are positioned in the same way as they are in FIG. 11 (A), but because the guide sheet 22 is in the shape of a cross, a portion of the upper surface of the absorber 14 and a portion of the upper surface of the surface sheet 10 are exposed in a different manner from FIG. 11 (A).

The back sheet 12 used is liquid-impermeable. There is no limit to the material, structure, etc. of the back sheet 12 as long as it is liquid-impermeable, and the same type of back sheet as the one used in the conventional absorbent products. The preferred examples are a single-layer synthetic resin film and a laminate of a synthetic resin film and a nonwoven fabric provided on the surface of the lower side of the synthetic resin film.

For the synthetic film, for example, there are a matted PE film and a porous air-permeable film. The air-permeable film is a synthetic resin film made porous by filler addition and polymer blending with its MVTR (Moisture Vapor Transmission Rate) indicating around 1000 to 6000 L/(m$^2$*24 hrs.). Typical air-permeable films include Espoir (manufactured by Mitsui Chemicals Inc.) and Porum (manufactured by Tokuyama Corp.), both manufactured by adding $CaCO_3$ as a filler to PE resin.

When the back sheet is composed of a single-layer synthetic resin film, it is preferred that the synthetic resin film is air-permeable, and when the back sheet is composed of a laminate of a synthetic resin film and nonwoven fabrics provided on the surface of the lower side of the synthetic resin film, it is preferred that both the synthetic resin film and the nonwoven fabrics are air-permeable. As described in these examples, when the back sheet has an air-permeable property, the comfortability of the wearer is improved. Furthermore, by using the stretchable composite sheet (such as the one described in JP 10-195746 A) in some or all parts of the back sheet, the fitting and the like are further improved.

It is preferred that the synthetic resin film composing the back sheet has concave and convex portions that form liquid trap portions on the surface of the upper side. Because the discharged liquid is first absorbed from the lower side and then later from the upper side of the absorber, the discharged liquid is uniformly diffused to the entire area of the lower side of the absorber by providing concave and convex portions on the back sheet.

As the configuration of concave and convex portions, the following can serve as examples: a configuration with a large number of projections, a configuration with grooves (such as V-shaped or U-shaped grooves), an imbricate configuration (as imbricate scales), and a ribbed configuration.

FIG. 12 is a set of illustrative top views, showing examples of the back sheet. The back sheet 12 in FIG. 12 (A) has a large number of grooves 30, forming concave portions. The back sheet 12 in FIG. 12 (B) has a large number of projections 32, forming convex portions.

One of the preferred embodiments of the back sheet is, precisely, a film processed to have concave and convex portions (for example, the one suggested in the specification of JP 2001-135239 A) wherein the synthetic resin film that constitutes the back sheet has concave and convex portions and has apertures in some of or in all of the convex portions, while the nonwoven fabric that constitutes the back sheet is a water-resistant laminate, of two layers or more, containing one layer or more of spunbond nonwoven fabrics and one layer or more of meltblown nonwoven fabrics.

As this kind of a laminate, the preferred examples include a laminate of film with apertured concave-and-convex portions and water-resistant SMS nonwoven fabric (nonwoven fabric of three-layer structure of spunbond/meltblown/spunbond) suggested in the specification of JP 2001-124237 A.

The positional relationship of the surface sheet 10, the absorber 14, and the back sheet 12 is explained below.

As described above, the back sheet 12 is positioned on the lower side of the absorber 14. More precisely, examples include, but are not limited to, positional relationships described below.

FIG. 13 is a set of illustrative cross-section views, each showing a portion of examples of the absorbent product. In FIG. 13, as a matter of explanatory convenience, only the surface sheet 10, absorber 14, the back sheet 12, and the guide sheet 22 are shown.

In FIG. 13 (A), the back sheet 12 covers the lower surface as well as both the right and left lateral surfaces of the absorber 14, whose upper surface is covered by the surface sheet 10.

In FIG. 13 (B), the back sheet 12 covers the lower surface, as well as both the right and left lateral surfaces of the absorber 14, whose upper surface is covered by the surface sheet 10 and furthermore, whose upper surface, both the right and left lateral surfaces and a portion of the lower surface are covered by the guide sheet 22.

FIG. 14 is an illustrative top view showing a portion of an example of the absorbent product. In FIG. 14, as a matter of explanatory convenience, only the surface sheet 10, absorber 14, and the back sheet 12 are shown.

In FIG. 14, the surface sheet 10 covers a portion of the upper surface of the absorber 14, and the back sheet 12 fully covers the absorber 14 and the lower surface of the surface sheet 10.

As the absorber, a conventional absorber may be used. More precisely, an absorber used in an absorbent product currently on the market, composed by wrapping a mixture of SAP and fluffy pulp with a liquid-permeable core-wrapping sheet made with material such as tissue paper, spunbond nonwoven fabric, and film with apertures is an example.

Also, for example, there is a highly water-absorbing sheet obtained by the Air Laid method. The air laid method is a method for obtaining a highly water-absorbing sheet by mixing pulverized pulp and SAP, adding a binding agent (such as a heat-sealed fiber) to the mixture, and shaping it into a sheet form and heating it. NOVATHIN, manufactured by Rayonier Inc. in the U.S., and KINOCLOTH, manufactured by Oji Kinocloth Co., Ltd., for example, are known as highly water-absorbing sheets obtained by this method.

There are also other examples, such as a highly water-absorbing sheet obtained by making SAP into dispersion slurry and the like, and by the method of coating to have the SAP held on at least one of two surfaces of a discharged-liquid-permeable sheet of a liquid-permeable nonwoven fabric and the like. This highly water-absorbing sheet is precisely described in the specification and other parts of JP 10-168230 A, the specification and other parts of JP 10-314217 A, and the specification and other parts of JP 2000-201975 A. The SAP dispersion slurry here is preferably a slurry obtained by dispersing SAP and Micro Fibrillated Cellulose (MFC) in a mixed solvent of water and ethanol. MEGATHIN, manufactured by Japan Absorbent Technology Institute, for example, is known as a highly water-absorbing sheet obtained by this method.

There are also other examples, such as a highly water-absorbing sheet obtained by the method of applying a large amount of SAP to fluffy nonwoven fabric, and settling it with a hot-melt binder, emulsion binder, water-soluble fiber, etc.; a highly water-absorbing sheet obtained by the method of mixing fibrous SAP and PET (polyethylene terephthalate) fibers, and forming the mixture into a web; as well as a highly water-absorbing sheet containing two layers of liquid-permeable nonwoven fabrics and SAP held in between the layers thereof.

It is preferred that the thickness of the highly water-absorbing sheet is 1.5 mm or less, and more preferably 1 mm or less.

It is preferred that the SAP content of the aforementioned absorber is 50 wt % or more of the content of the absorber, and more preferably 60 to 95 wt % of the content of the absorber.

The absorbent product, as described below, may have a plural number of absorbers, but when a mixture of SAP and fluffy pulp is used as an absorber as described above, it is bulky, and while absorbing capacity is great, retention is relatively small, so a single layer of the mixture is usually used. The conventional absorbent product which uses an absorber such as this have a great re-wet amount, but in the disclosure, a liquid-impermeable surface sheet is used, and thus, may decrease the re-wet amount to a small percent of that of the conventional absorbent products.

At the same time, when the aforementioned highly water-absorbing sheet is used, because the highly water-absorbing sheet is extremely thin with relatively high retention compared to the absorption capacity, and its demand wettability is high, one of the preferred embodiments, as suggested in JP 2002-113800 A, is structured with a multiple layer of a plural number of absorbers, and which has the discharged liquid absorbed by the absorber starting at the lower layer and gradually at higher layers.

Next, the embodiments of the absorbent product are explained below.

The absorbent product can be easily obtained by using a conventional absorbent product such as a tape-type and a pull-on type (pants-type) baby diaper and adult incontinence diaper, a sanitary napkin for women, and other incontinence products. In other words, an absorbent product with significantly improved performance can be obtained by inserting a surface sheet, preferably a surface sheet combined with a guide sheet, in between a top sheet and an absorber of a conventional absorbent product.

One of the preferred embodiments of the absorbent product is an absorbent product including an absorbent product main body that can form an internal space to contain the wearer's objective region when worn; housing for an absorber unit adjacent to the absorbent product main body to communicate to the internal space, and containing the back sheet on the inner walls thereof; and an absorber unit structured by combining at least the surface sheet and the absorber, being received removably by the housing for the absorber.

Figure 15:
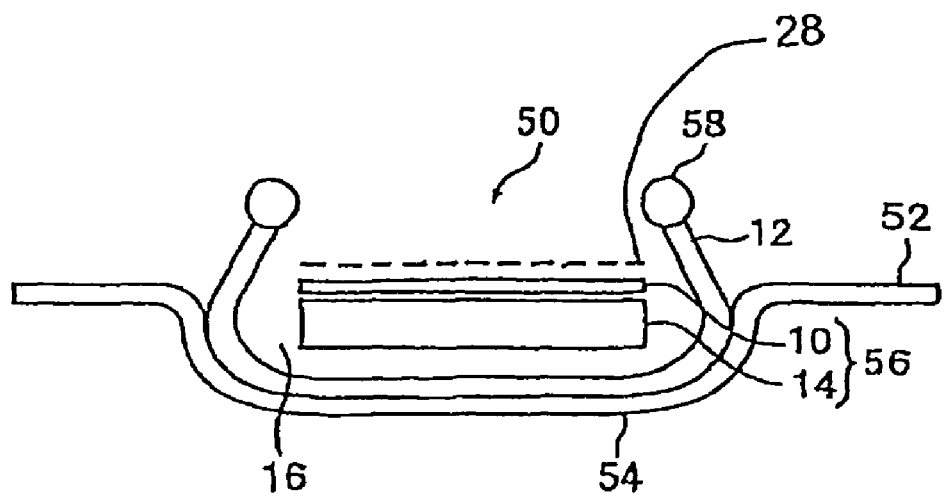
FIGS. 15(A)-(C) are a set of illustrative cross-section views showing examples of a portion of the absorbent product.

FIG. 15 is a set of illustrative cross-section views showing examples of a portion of the aforementioned absorbent product.

The absorbent product 50 shown in FIG. 15 (A) includes an absorbent product main body 52 that can form an internal space to contain the wearer's objective region when worn; housing for an absorber unit 54 adjacent to the absorbent product main body 52 to communicate to the internal space, and containing the back sheet 12 on the inner walls thereof; and an absorber unit 56 formed by the surface sheet 10 and the absorber 14, removably received by the housing for the absorber unit 56. Note that only a part of the absorbent product main body 52 is shown, and the space in upper side of the drawing represents the aforementioned inner space. The surface sheet 10, back sheet 12 and the absorber 14 are as described above.

In FIG. 15 (A), the member constituting the absorbent product main body 52 also constitutes housing for an absorber unit 54, and a back sheet 12 constituted by another member is provided inside the housing for an absorber unit 54. It is acceptable as long as the housing for an absorber unit contains a back sheet inside thereof, and the member constituting the back sheet, for example, may also constitute the housing for an absorber unit.

As the absorbent product main body 52, an absorbent product main body comprising a laundry-proof material that can be used plural times, such as a conventional diaper cover, may be used. It is preferred that the absorbent product main body 52 is a plain knit product such as a stockinet knit product, because it improves the fitting when worn.

On both the right and left end portions of the back sheet 12 shown in FIG. 15, side-gather members 58 are provided. The structure of the side-gather members 58 may be a conventional structure, comprising a bundle of polyurethane filament, elastic film, etc.

The absorbent product 51 shown in FIG. 15 (B) is the same as the absorbent product 50, except that the latter includes the guide sheet 22 as shown in the drawing. An internal space is formed when a wearer is wearing the absorbent product 51.

The absorbent products 50 and 51 shown in FIGS. 15 (A) and (B) have the absorbent product main body 52 and the housing for the absorber unit 54 directly communicated to each other (in other words, the surface sheet 10 or the guide sheet 22 is exposed), but the aforementioned liquid-permeable skin-contact sheet 28 may be included in at least a portion of the space of these two as shown in FIG. 15(C).

In FIG. 15, one absorber unit is housed in the housing for the absorber unit 54, but as described below, a laminated plural number of absorber units may also be housed.

One of the preferred embodiments of the absorbent product is an absorbent product which includes a main body made of an absorbent product that can form an internal space to contain the wearer's objective region when worn; housing for an absorber adjacent to the absorbent product main body to communicated to the internal space and containing the back sheet on the inner walls thereof; an absorber, being received removably by the housing for the absorber; and a surface sheet contained at least in a portion of the space between the absorbent product main body and the housing for the absorber.

FIG. 16 is an illustrative top view showing a portion of an example of the aforementioned absorbent product.

The absorbent product 60 shown in FIG. 16 includes an absorbent product main body 52 that can form an internal space to contain the wearer's objective region when worn; housing for an absorber 55 adjacent to the absorbent product main body 52 to communicate to the internal space, and containing the back sheet (not shown) on the inner walls thereof; an absorber 14 received removably by the housing for the absorber 55, and the surface sheet 10 attached to the housing for the absorber 55 to wrap the absorber 14 over the upper surface thereof. Note that only a part of the absorbent product main body 52 is shown, and the space in upper side of the drawing represents the aforementioned inner space. The surface sheet 10, back sheet 12 and the absorber 14 are as described above.

As long as the housing for an absorber contains a back sheet inside thereof it is acceptable; for example the member constituting the absorbent product main body may constitute the housing for an absorber 55, a back sheet may be constituted inside the housing for an absorber with another different member, and the member constituting the back sheet may also constitute the housing for an absorber.

Figure 17:
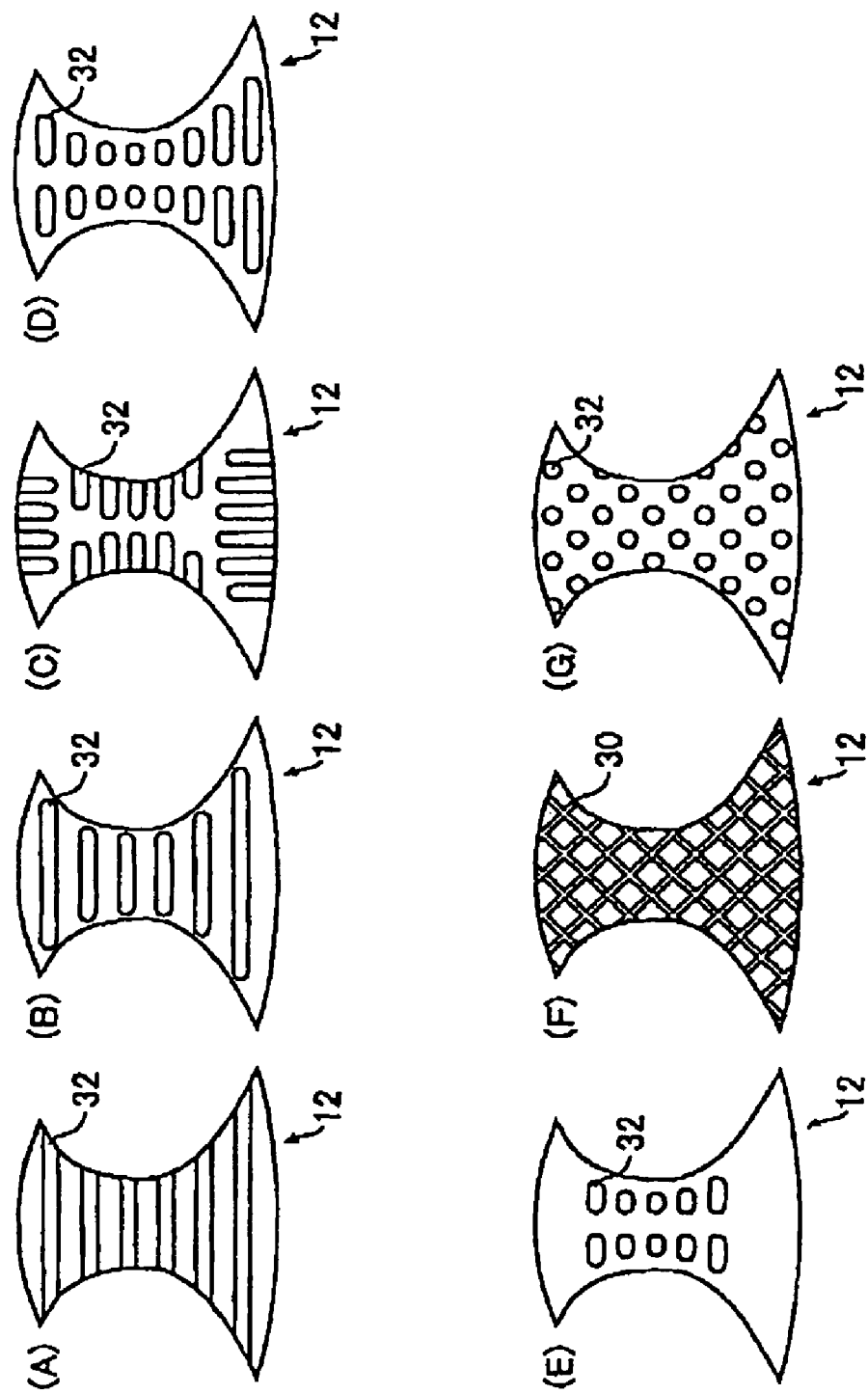
FIGS. 17(A)-(G) are a group of illustrative top views, each showing an example of preferred configuration of the back sheet when the member constituting the back sheet itself constitutes the housing.

FIG. 17 is a group of illustrative top views, each showing an example of preferred configuration of the back sheet when the member constituting the back sheet itself constitutes the housing for the absorber. In a structure such as this, it is preferred that a durable and water-resistant material such as GORE-TEX, for example, is used as a back sheet.

Every back sheet 12 in FIGS. 17 (A) through (E) has a large number of projections 32, forming convex portions. The back sheet 12 in FIG. 17 (F) has a large number of linear grooves 30, forming concave portions. Quilted cloth, for example, may be used. The back sheet 12 in FIG. 17 (G) has a large number of dot-like projections 32, forming convex portions.

The absorbent product main body 52 and the side-gather member 58 are the same as those of the absorbent product 50 shown in FIG. 15.

Also, even if the back sheet is constituted with a different material inside of the housing for the absorber, the same effect as in the case concavity and convex are provided on the back sheet will be obtained, by providing concave and convex portions on the profile of the member comprising the housing for the absorber, and achieving the effect of concave and convex portions on the back sheet that is laminated on it.

The absorbent product 60 with the aforementioned guide sheet laminated on the surface of the upper side surface sheet 10 is one of the preferred embodiments as shown in FIG. 16(B). In this embodiment, the guide sheet may be laminated so as to cover the surface sheet over the upper side thereof, as well as to wrap the lateral surfaces of the absorber from the lower side thereof.

Also, the absorbent product 60 may include a liquid-permeable skin-contact sheet, same as in the case of the absorbent products 50 and 51 as shown in FIG. 16(C).

Furthermore, the absorbent product 60 may house a plural number of laminated absorbers 14, as described below.

One of the preferred embodiments of the absorbent product, as described above, includes laminated plural pieces of absorber units or absorbers as shown in FIG. 16(D). A thin and compact absorber with high SAP content, when for instance the aforementioned highly water-absorbing sheet is used, is especially preferred.

There is no limit in particular to the number of the absorber units or the absorbers in the laminate, as long as the laminate has two layers or more, but it is preferred that the laminate has 5 layers or less. As long as the number of layers does not exceed 5, it prevents a compact absorbent product from becoming too bulky.

FIG. 18 (A) is an illustrative cross-section view showing an example of laminated plural pieces of absorber units. FIG. 18 (B) is an illustrative cross-section view showing an example of laminated plural pieces of absorbers. In FIG. 18 (A), three layers of laminated absorber units 56 are shown. In FIG. 18 (B), three layers of laminated absorbers 14 are shown.

FIG. 18 (C) is an illustrative cross-section view showing an example of a portion of the absorbent product, including laminated plural number of absorber units. The absorbent product 70 shown in FIG. 18 uses the absorber unit 56, which is in a single layer in the absorbent product 50 shown in FIG. 5 (A), by laminating them in three layers as shown in FIG. 18 (A).

When the absorbent product is used by laminating them in multiple layers, use of more than once is possible, corresponding to the number of layers, reducing the frequency of exchange of the absorbent product, for example from three to five times a day to once or twice a day. The reason why use more than once is possible is explained below.

In the absorbent product, as mentioned above, the discharged liquid is absorbed mainly from the lower side of the absorber, and then is diffused to the upper side. The majority of the discharged liquid is absorbed from the lower-most absorber. And then, after being absorbed from the lower-most absorber to the limit of or in the vicinity of the limit of its absorbing capacity, the discharged liquid is absorbed into the second absorber from the bottom. In this way, absorbing of the discharged liquid progresses from the bottom to the top, until the absorbing capacity of the upper-most absorber reaches the limit. Therefore, by separating the absorber which has absorbed the discharged liquid to the limit of its absorbing capacity from the rest individually at the proper time, use of more than once becomes possible. In this way, not only feelings of bulkiness or of weight felt by the wearer is eliminated, but also the lowering of the absorbing capacity, caused by the pressure from the weight of the absorber with its absorbed discharged liquid, is prevented.

In contrast to this, if an absorbent product that uses a conventional liquid-permeable top sheet is made into multiple layers, absorbing action progresses from the top to the bottom, but before the discharged liquid is absorbed to the limit of the absorbing capacity of the absorber on the upper side, absorbing into the absorber below it begins. Thus, the discharged liquid is absorbed by all the absorbers, especially in the portion in the center, when viewed from above the surface where the discharged liquid is supplied. As described above, because all the absorbers start swelling gradually in the initial stage of use, and as a result, the discharged liquid does not diffuse entirely in the individual absorber, separating an individual absorber from the rest does not work. Separation in this case will extremely worsen the rate of utilization. And because separation of the absorber individually from the rest is not possible, it ends up becoming heavy. Therefore, making a multiple-layer absorbent product with a conventional absorbent product is not realistic.

Furthermore, in the absorbent product, even if plural number of absorbers are used, the re-wet amount will be extremely small, as in the case of a single-layer absorber; and the upper surface of the upper-most absorber will stay from the start of use till right before the end of use as dry as it is before use, leading to improved comfortability for the wearer.

There is no limit in particular to the structure enabling the separation of the used absorber from the rest, but the structure comprising an aperture portion, preferably an aperture portion in the outer space at the housing for the absorber unit or the housing for the absorber may be an example. The structures suggested in the specification of JP 2002-233209 A are suitable for use.

Especially, the structure that includes a member for pulling out is preferred. The structure described in JP 7-12117 U has one of the preferred examples of this member for pulling out.

FIG. 19 is a group of explanatory drawings, each showing an example of the absorbent product with a member for pulling out. FIG. 19 (A) is a top view, FIG. 19 (B) is a longitudinal section view, and FIG. 19 (C) is a longitudinal section view of the absorbent product including the absorber. In FIGS. 19 (B) and (C), the left side of the drawing is the front side of the absorbent product and the right side of the drawing is the back side of the absorbent product. In FIGS. 19 (A) to (C), the back sheet is not shown and M represents the body of a wearer.

The absorbent product 80 shown in FIG. 19 has a member for pulling out 62, which is in a tape form, positioned in the upper portion of the front end of the absorber 14. It is preferable if the member for pulling out 62 has an adhesive layer 64 on its lower surface. In that case, it is preferred that a release layer 66 is provided in the portion corresponding to the adhesive layer 64, and that the release layer 66 is in close contact with the surface of the adhesive layer 64 before it is incorporated in the absorbent product 80. In the absorber 14, housed in the housing for absorber units 54 of the absorbent product 80, the member for pulling out 62 extends from the aperture portion of the housing for the absorber unit 54 to outside of it, and then to the absorbent product main body 52 side, and the member for pulling out 62 is fixed on the absorbent product main body 52 with the adhesive layer 64. After the lower-most absorber 14 absorbs the discharged liquid to the limit of its absorbing capacity, the lower-most absorber 14 can be easily separated from the rest by pulling out this member for pulling out 62.

In addition to a surface sheet, a back sheet, and an absorber, the absorbent product may include such members as gazette gathers, standing gathers, waist gathers, a fastening mechanism (tape, hook-and-loop fastner, etc.), and the wrapping tape mechanism used at the time of disposal. For these, conventional ones may be used.

The absorbent product is suitable for use in baby diapers, adult incontinence diapers, sanitary napkins for women, etc.

When the absorbent product is used as a diaper, it may be used for urine-disposing only or for both urine- and feces-disposing. When it is used for both urine- and feces-disposing, it is preferred that a urine-disposing portion extending from the center portion to the front body section, and a feces-disposing portion extending from the center portion to the back body section are provided, and that the surface sheet is provided only at the urine-disposing portion.

Figure 20:
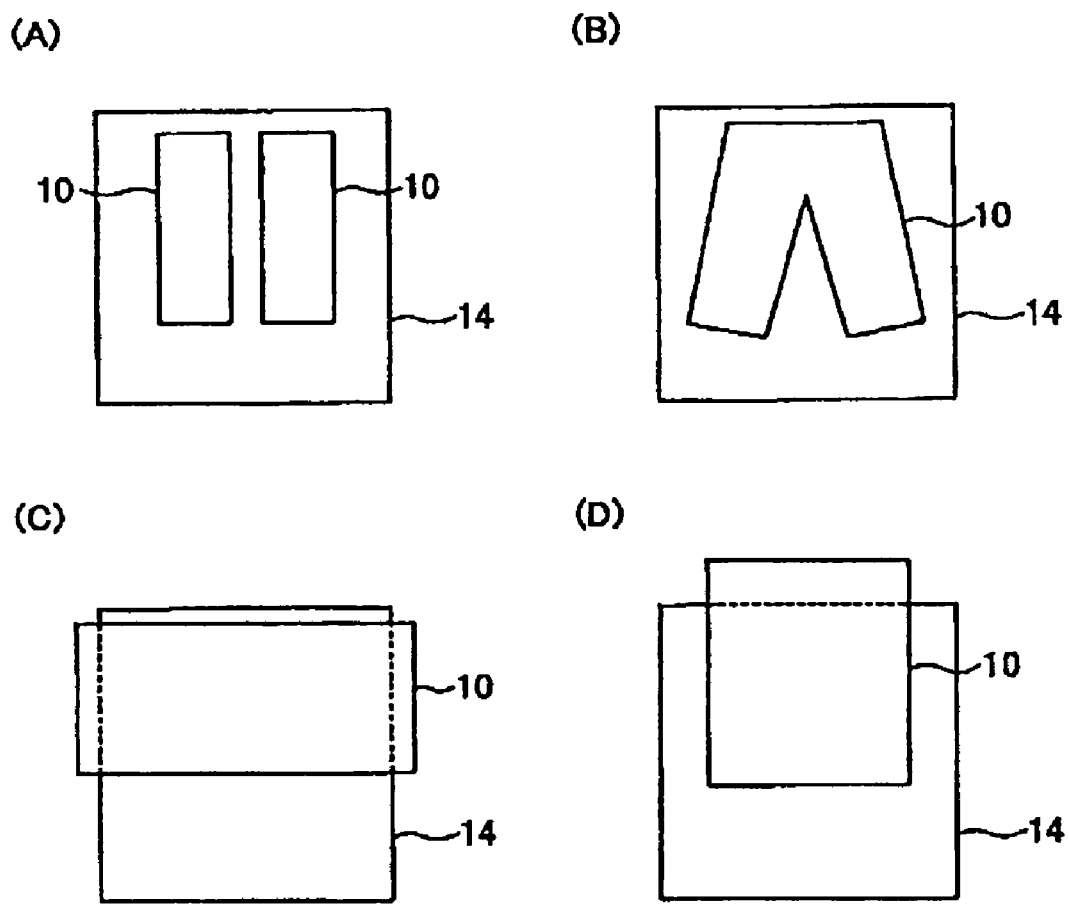
FIGS. 20(A)-(D) are a group of illustrative top views, each showing an example of a portion of the absorbent product.

FIG. 20 is a group of illustrative top views, each showing an example of a portion of the absorbent product. In FIGS. 20 (A) through (D), the upper side of the drawing is the front side of the absorbent product and the lower side of the drawing is the back side of the absorbent product.

In all of FIGS. 20 (A) through (D), the surface sheet 10 is provided only in the urine-disposing portion at the front side of the absorber 14, and is not provided in the feces-disposing portion at the back side.

As for the structures that are different in the front side and the back side of the absorber, and as for the manufacturing method, one of the preferred embodiments is to use the technology described in JP 6-343660 A. When this kind of structure is adopted, leg gathers or the like may be provided only at the front side.

Mixing of urine and feces is one of the causes of odor and rashes. A means to separate urine and feces, such as the urine-feces separator described in the JP 7-299092 A, may be applied to the absorber.

Figure 21:
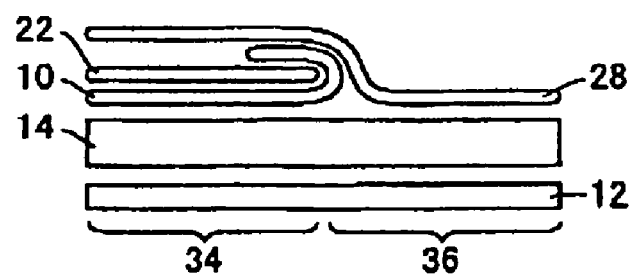
FIG. 21 is an illustrative longitudinal section view showing an example of a portion of the absorbent product.

FIG. 21 is an illustrative longitudinal section view showing an example of a portion of the absorbent product. In FIG. 21, the left side of the drawing is the front side of the absorbent product and the right side of the drawing is the back side of the absorbent product.

In FIG. 21, the surface sheet 10 is provided only in the urine-disposing portion 34 at the front side of the absorber 14, and is not provided in the feces-disposing portion 36 at the back side. The surface sheet 10 is folded on a guide sheet 22 in the vicinity of the border between the urine-disposing portion 34 and the feces-disposing portion 36 of the absorber 14, and the folded portion can temporarily retain the urine to prevent the discharged liquid (urine) discharged at the urine-disposing portion from moving to the feces-disposing portion 36.

It is preferred that the absorbent product comprising the urine-disposing portion and the feces-disposing portion includes, at least at the feces-disposing portion, a liquid-impermeable or water-resistant urine backflow prevention sheet inside and/or on the upper surface thereof.

Figure 22:
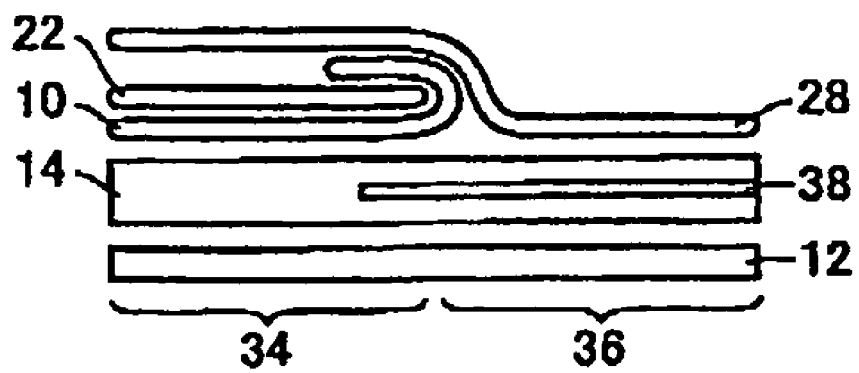
FIG. 22 is an illustrative longitudinal section view showing an example of a portion of the absorbent product.

FIG. 22 is an illustrative longitudinal section view showing an example of a portion of the absorbent product. In FIG. 22 the left side of the drawing is the front side of the absorbent product and the right side of the drawing is the back side of the absorbent product.

The absorbent product shown in FIG. 22 includes, at the feces-disposing portion 36, a liquid-impermeable or water-resistant urine backflow prevention sheet 38 inside the absorber 14. This urine backflow prevention sheet 38 is explained below.

In case the absorbent product does not include the urine backflow prevention sheet 38 as shown in FIG. 21, the surface sheet 10 can prevent the urine from moving on the upper side of the absorber 14 from the urine-disposing portion 34 to the feces-disposing portion 36, but the urine absorbed from the lower side of the absorber 14 can sometimes penetrate to the upper side of the absorber 14, reaching the surface of the upper side of the feces-disposing portion 36. In other words, the urine sometimes flows back. When this occurs, the effect of separating the urine and the feces disappears, and problems such as dirtying the buttocks and developing of diaper rashes can take place.

In contrast to this, in case the absorbent product includes the urine backflow prevention sheet 38 as shown in FIG. 22, the surface sheet 10 prevents the urine from moving on the upper side of the absorber 14 from the urine-disposing portion 34 to the feces-disposing portion 36, and in addition to this, even if the urine absorbed from the lower side of the absorber 14 penetrates to the upper side of the absorber 14, because a liquid-impermeable or water-resistant urine backflow prevention sheet 38 is provided inside the absorber 14, the urine will be prevented from reaching the surface of the upper side of the feces-disposing portion 36. In other words, the urine is prevented from flowing back. The desirable result of being free from the above problems is obtained.

There is no limit in particular to the material, structure, etc. of the urine backflow prevention sheet 38, as long as it is liquid-impermeable or water-resistant, and the film similar to the aforementioned surface sheet 10 and the back sheet 12, as well as a water-resistant nonwoven fabric may be used. In this specification, "water-resistant" means the characteristic that does not allow the water to permeate at a pressure of 100 mmH$_2$O (9.807×10$^2$ Pa) or lower. It is preferred that the water-resistant nonwoven fabric has water resistance at a pressure of 200 mmH$_2$O (1.961×10$^3$ Pa) or lower.

It is preferred that the urine backflow prevention sheet 38 is provided in a manner covering at least the feces-disposing portion 36 in the anteroposterior direction of the absorber 14 as described in FIG. 22. Furthermore, also in the left-to-right direction of the absorber 14, it is preferred that it covers the feces-disposing portion 36 to prevent the urine from reaching the surface of the upper side of the absorber 14.

The urine backflow prevention sheet 38 is provided inside the absorber 14 in FIG. 22, but it can also be provided on the surface of the feces-disposing portion 36, as well as at both of the above. Furthermore, plural sheets may be provided. There is no limit in particular to the method of providing the urine backflow prevention sheet 38 inside the absorber 14. If, for example, the absorber 14 is composed of laminating plural number of highly water-absorbing sheets, the urine backflow prevention sheet 38 may be held in between these highly water-absorbing sheets.

As mentioned above, the absorbent product is significantly different from the conventional absorbent products in the way a part of or all of the discharged liquid supplied to the surface sheet moves downward. This will be explained further in detail.

Figure 23:
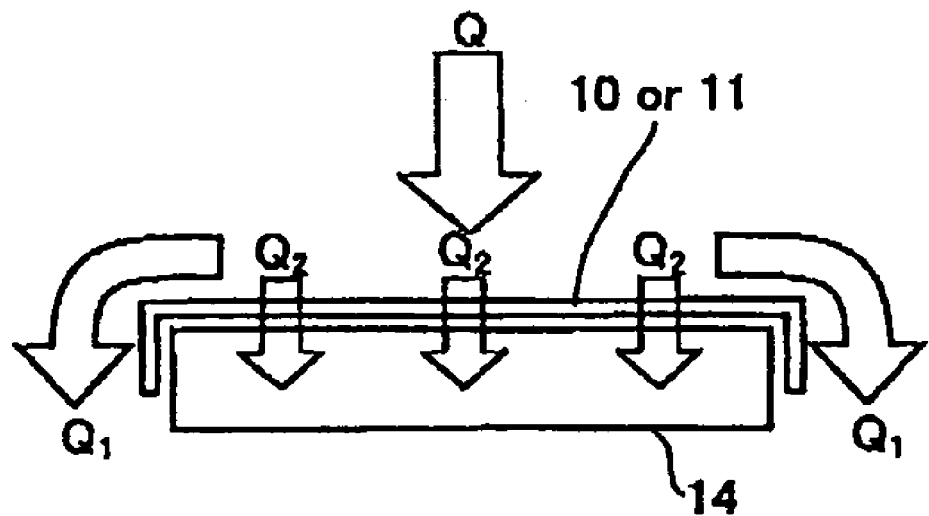
FIG. 23 is a cross-section view explaining the behavior of the discharged liquid when it is supplied to an absorbent product.

FIG. 23 is a cross-section view explaining the behavior of the discharged liquid when it is supplied to an absorbent product. In FIG. 23, only the absorber 14 and the sheet fully covering it in a left-to-right direction (this sheet is the liquid-permeable top sheet 11 in the conventional absorbent product, and is the liquid-impermeable surface sheet 10 in the absorbent product) are shown.

The total amount of discharged liquid supplied to the sheet 10 or sheet 11 is denoted by Q, the total amount of the discharged liquid absorbed from the lateral surfaces or the lower surface by $Q_1$, and the total amount of the discharged liquid absorbed from the upper surface by $Q_2$ (provided that $Q=Q_1+Q_2$).

In the conventional absorbent product, because nearly total amount of the discharged liquid supplied to the top sheet 11 passes through the top sheet 11 and absorbed by the absorber 14, most commonly $Q_1$ is approximately 1 to 10%, $Q_2$ is approximately 99 to 90%, and $Q_1/Q_2$ is approximately 0.01 to 0.1.

In contrast to this, in an embodiment of the absorbent product wherein the surface sheet 10 fully covers the upper surface of the absorber 14 (for example, the absorbent product shown in FIGS. 7 (A) and (B)), because nearly the total amount of the discharged liquid supplied to the surface sheet 10 moves on the upper surface of the surface sheet 10 to the lower side of the absorber 14 via the end portions of the surface sheet 10, most commonly $Q_1$ is approximately 90 to 99%, $Q_2$ is approximately 10 to 1%, and $Q_1/Q_2$ is approximately 9 to 99.

Furthermore, in an embodiment of the absorbent product wherein the surface sheet 10 covers a portion of the upper surface of the absorber 14 (for example, the absorbent product shown in FIGS. 7 (C) through (G)), because a part of the discharged liquid supplied to the surface sheet 10 moves on the upper surface of the surface sheet 10 to the lower side of the absorber 14 via the end portions of the surface sheet 10 and the remaining amount is absorbed directly from the upper surface of the absorber 14 with the portion thereof being exposed, though it depends on the design, $Q_1$ is approximately 50 to 70%, $Q_2$ is approximately 50 to 30%, and $Q_1/Q_2$ is approximately 1.0 to 2.5, for example.

As described above, the absorbent product is significantly different from the conventional absorbent products in terms of its discharged-liquid-absorbing mechanism, and as a result, prevention of absorbing rate from lowering with the elapse of time and reduction of the re-wet amount are realized.

Hereinafter, the effect will be explained further in detail by using the Examples.

EXAMPLES

1. Absorbing Rate and Re-Wet Amount of Absorbent Products (1) Preparation of Absorbent Products Example 1

The absorber was taken from a commercially available diaper, Kao Corporation's Merries, with a top sheet adhered thereto.

As shown in FIG. 24, the absorber 14 taken out of the diaper was turned upside down and was covered with an air-permeable PE film (manufactured by Tokuyama Corp., in a thickness of 20 μm) used as a back sheet in commercially available diapers, which was used here to function as the liquid-impermeable surface sheet 10.

The upper surface, lateral surfaces and a portion of the lower surface of the absorber 14 were covered with a porous PE film (manufactured by Tredeger Co. and marketed as "T10650-1 TEC") which was used here to function as the guide sheet 22.

Furthermore, the absorber was covered with an air-permeable PE film (manufactured by Tokuyama Corp., in a thickness of 20 μm) used as a back sheet in commercially available diapers, which was used here to function as the liquid-impermeable back sheet 12, and the absorbent product 90 was obtained.

Example 2

By the same method used in Example 1, except that Unicharm Corporation's Mamypoko-Cotton was used here as a commercially available diaper, the absorbent product 90 was obtained.

Example 3

By the same method used in Example 1, except that a prototype diaper using MegaThin (a highly water-absorbing sheet), an absorber manufactured by Japan Absorbent Technology Institute, was used here instead of a commercially available diaper, the absorbent product 90 was obtained.

Note that Kao Corporation's Merries, Unicharm Corporation's Mamypoko-Cotton, and a prototype diaper using MegaThin, the absorber manufactured by Japan Absorbent Technology Institute were used as they are as Comparative Examples 1 through 3 for measuring the absorbing capacity and re-wet amount, as hereinafter described.

(2) Measuring of Absorbing Capacity

As described below, the absorbing capacity of each absorber of the 2 types of commercially available diapers and one prototype diaper used in the Examples 1 through 3 was measured.

The diapers whose weights were measured beforehand were soaked in a sodium chloride solution of 0.9 wt % for 30 minutes. After that, the diapers were taken out of the solution and kept in the condition of just being taken out of the solution for 30 seconds and drained. They were placed on a wire-mesh drainer with their top sheet facing down, an acrylic plate was placed on top of them to apply load to the absorbers in their entirety, and furthermore a weight (10 kg) was put on top of the acrylic plate, after which they were left to stand for 20 minutes, and then drained. After that, they were weighed, and the increased weight was defined as the absorbing capacity. (The specific gravity of the sodium chloride solution was assumed to be 1.) The measurement was made under the condition of n=2. The absorbing capacity of the absorber of Kao Corporation's Merries was 707 mL, that of Unicharm Corporation's Mamypoko-Cotton was 606 mL, and of that of a prototype diaper using MegaThin, the absorber manufactured by Japan Absorbent Technology Institute was 756 mL.

(3) Measuring of Absorbing Rate

The absorbing rate of each of the absorbent products of Examples 1 through 3 and Comparative Examples 1 through 3 was measured as described below.

As shown in FIG. 25, a liquid-supplying plate (made of plastic and 7.5 cm×10 cm in size) 92, comprising a cylindrical liquid-supplying portion with 2.0 cm inside diameter, and a weight 94 positioned in the periphery of the liquid-supplying portion, was placed in the center of the upper surface of the absorbent product 90, and a load of 0.1 psi ($6.895 \times 10^2$ Pa) was applied. Note that FIG. 25 (A) is a perspective view and FIG. 25 (B) is a longitudinal-section view.

100 mL sodium chloride solution of 0.9 wt % was supplied to the liquid-supplying portion, and the time until it was visually confirmed that the sodium chloride solution inside the liquid-supplying portion had disappeared was measured. This time-measuring exercise was repeated three times in such a manner that the respective supplies of the liquid began in every 10 minutes.

The results are shown in Table 1.

TABLE 1

|  |  | Com. Ex. 1 | Ex. 1 | Com. Ex. 2 | Ex. 2 | Com. Ex. 3 | Ex. 3 |
| --- | --- | --- | --- | --- | --- | --- | --- |
| Absorbing Rate (sec.) | $1^{st}$ Time | 28 | 11 | 49 | 17 | 18 | 12 |
|  | $2^{nd}$ Time | 35 | 12 | 81 | 16 | 14 | 14 |
|  | $3^{rd}$ Time | 43 | 13 | 102 | 16 | 16 | 15 |
| Average of 3 measurements (sec.) |  | 35 | 12 | 77 | 16 | 16 | 14 |
| Standard Deviation of 3 measurements (sec.) |  | 6.1 | 0.8 | 21.8 | 0.5 | 1.6 | 1.2 |

As evident in Table 1, the absorbent products (Example 1 through 3) had dramatically higher absorbing rates than the conventional absorbent products (Comparative Examples 1 through 3), and furthermore their absorbing rates hardly changed with the elapse of time. Especially, when a mixture of SAP and fluffy pulp was used as an absorber, conventionally, the absorbing rate was low and the change of the absorbing rate with the elapse of time was significant (Comparative Examples 1 and 2), but they were markedly improved in the absorbent products of the present disclosure (Examples 1 and 2).

(4) Measuring of Re-Wet Amount (a) Re-Wet Amount Per 100 mL of Supplied Liquid The re-wet amount of the absorbent products per 100 mL of supplied liquid in Examples 1 and 3 and Comparative Examples 1 and 3 was measured in the way described below.

Under no load, 100 mL of sodium chloride solution of 0.9 wt % was added dropwise at the rate of 13 mL/sec onto the center of the upper surface of the absorbent product by using a burette positioned at 10 mm above the surface. Five minutes later from the start of dripping the solution, a paper filter whose weight was measured beforehand was placed in such a way that its center matched the spot where the solution was added dropwise, and a weight was put on top of it to apply a load of 0.1 psi ($6.895 \times 10^2$ Pa). Three minutes later, the weight was removed, the paper filter was weighed and the measurements of the re-wet amount per 100 mL of supplied liquid. This process was repeated a total of seven times in such a manner that dropwise addition of the solution began in every 10 minutes.

The results are shown in Table 2.

TABLE 2

|  |  | Comparative Example 1 | Example 1 | Comparative Example 3 | Example 3 |
| --- | --- | --- | --- | --- | --- |
| Re-wet Amount (mL) | $1^{st}$ Time | 0.3 | 6.1 | 0.6 | 0.6 |
|  | $2^{nd}$ Time | 8.2 | 3.8 | 0.7 | 0.1 |
|  | $3^{rd}$ Time | 16.7 | 1.5 | 0.4 | 2.8 |
|  | $4^{th}$ Time | 23.2 | 2.2 | 3.3 | 0.1 |
|  | $5^{th}$ Time | 25.9 | 0.6 | 12.6 | 0.3 |
|  | $6^{th}$ Time | 39.5 | 1.9 | 22.3 | 0.6 |
|  | $7^{th}$ Time | 49.1 | 0.7 | 41.0 | 0.6 |
| Average of First 3 measurements (mL) |  | 8.4 | 3.8 | 0.6 | 1.2 |
| Standard Deviation of First 3 measurements (mL) |  | 6.7 | 1.9 | 0.1 | 1.2 |

TABLE 2-continued

|  | Comparative Example 1 | Example 1 | Comparative Example 3 | Example 3 |
|---|---|---|---|---|
| Average of 7 measurements (mL) | 23.3 | 2.4 | 11.6 | 0.7 |
| Standard Deviation of 7 measurements (mL) | 15.7 | 1.8 | 14.2 | 0.9 |

(b) Re-Wet Amount when the Amount of Liquid Equivalent to ½ of the Absorbing Capacity is Supplied (when 50% is Supplied)

The re-wet amount of the absorbent products in each Examples 1 through 3 and Comparative Examples 1 through 3 was measured when the amount of liquid equivalent to ½ of the absorbing capacity was supplied, as described below.

Under no load, 100 mL of sodium chloride solution of 0.9 wt % was added dropwise at a rate of 13 mL/sec onto the center of the upper surface of the absorbent product by using a burette positioned 10 mm above the surface. This was repeated in such a manner that the dropwise addition of the solution began in every 5 minutes, until the amount of the solution added dropwise reached an amount equivalent to ½ of the absorbing capacity (350 mL in Examples 1 and 3 and Comparative Examples 1 and 3, and 300 mL in Example 2 and Comparative Example 2). Note that when ½ of absorbing capacity was 350 mL, the amount of sodium chloride solution added dropwise at the fourth time was 50 mL. Five minutes later from the beginning of dropwise addition of the solution of the last round, a paper filter whose weight was measured beforehand was placed in such a way that its center matched the spot where the solution was being added dropwise, and a weight was put on top of it to apply a load of 0.1 psi ($6.895 \times 10^2$ Pa). Three minutes later, the weight was removed, the paper filter was weighed and the measurements of the re-wet amount when an amount of liquid equivalent to ½ of the absorbing capacity is supplied were made.

The re-wet amount was measured three times in this manner, and the average value was calculated.

Furthermore, the weight was changed to apply a load of 0.5 psi ($3.448 \times 10^3$ Pa), and the re-wet amount when the amount of liquid equivalent to ½ of the absorbing capacity is supplied was measured three times in the same method and the average value was obtained.

The results are shown in Table 3.

TABLE 3

| Load (psi) | Comparative Example 1 | Example 1 | Comparative Example 2 | Example 2 | Comparative Example 3 | Example 3 |
|---|---|---|---|---|---|---|
| 0.1 | 24.1 | 0.5 | 34.1 | 0.1 | 3.3 | 0.1 |
| 0.5 | 37.3 | 0.6 | 39.3 | 0.8 | 10.0 | 1.5 |

As evident in Table 2 and Table 3, the absorbent products (Examples 1 through 3) had a dramatically smaller re-wet amount than the conventional absorbent products (Comparative Examples 1 through 3), and furthermore their re-wet amount hardly changed with the elapse of time.

2. Characteristics of the Absorbent Product Including a Plural Number of Absorber Units (1) Preparation of Absorbent Products Example 4 and Comparative Examples 4 and 5

The absorbent products 100 including a plural number of absorber units as shown in FIG. 26 were made. As the absorbent product main bodies 52, sewn stockinet underpants for women (manufactured by Gunze Ltd.), to which the housing for the absorber, including the leak-proof back sheet, was attached, were used. FIG. 26 (A) is a front view and FIG. 26 (B) is a top view. In FIG. 26 (A), this side of the drawing is the front side of the absorbent product.

The absorbent products 100 were obtained by housing the laminates shown in FIG. 28, which are obtained by laminating 3 pieces of each absorber unit shown in FIG. 27, in the housing for the absorber units 54 in the absorbent product main body 52. All views shown in FIG. 27 and FIG. 28 are cross-section views.

The absorber unit used in Example 4, as shown in FIG. 27 (A), was obtained by covering with the liquid-impermeable surface sheet 10, the upper surface, lateral surfaces and a portion of lower surface of the absorber 14 made by folding in half the super absorbent sheet comprising a SAP layer 102 on one side of it, in such a manner that the SAP surface faces inside of the fold.

The absorber unit used in Comparative Example 4, as shown in FIG. 27 (B), was obtained by covering with the liquid-permeable sheet 104, the lower surface, lateral surfaces and a portion of the upper surface of the absorber 14 same as the one used in Example 4.

The absorber unit used in Comparative Example 5, as shown in FIG. 27 (C), was obtained by covering with the liquid-permeable sheet 104, instead of the liquid-impermeable surface sheet 10 used in Example 4.

In the Example 4, three pieces of the absorber unit shown in FIG. 27 (A) were laminated and used (from the top, each layer is called the first layer, second layer, and the third layer). The areas between the first layer and the second layer, as well as between the second layer and the third layer, were adhered in a quick and simple manner by providing a hot-melt layer 106 at their left and right end portions. The upper surface, lateral surfaces and most of the lower surface of the laminate of the three absorber units were covered with the guide sheet 22 and used.

In the Comparative Example 4, three pieces of the absorber unit shown in FIG. 27 (B) were laminated and used (from the top, each layer is called the first layer, second layer, and the third layer). The areas between the first layer and the second layer, as well as between the second layer and the third layer, were adhered in a quick and simple manner by providing a hot-melt adhesive layer 106 at their left and right end portions.

In the Comparative Example 5, three pieces of the absorber unit shown in FIG. 27 (C) were laminated and used (from the top, each layer is called the first layer, second layer, and the third layer). The areas between the first layer and the second layer, as well as between the second layer and the third layer, were adhered in a quick and simple manner by providing a hot-melt adhesive layer 106 at their left and right end portions.

(2) Absorbability Test

The absorbent products of Example 4 and Comparative Examples 4 and 5 were actually put on a wearer, and the wearer urinated twice, each time in a standing position. The second urination was performed after one predetermined layer of the absorber was removed following the first urination. The amount of urine discharged each time was about 200 mL. The amount absorbed by each layer of the absorber after each urination was measured and the rate of utilization was calculated.

The results after the first urination of Example 4 are shown in Table 4.

TABLE 4

| Layer | Actual Amount Absorbed (mL) | Designed Absorption Amount (mL) | Rate of Utilization (%) |
|---|---|---|---|
| 1$^{st}$ Layer | 0 | 200 | 0 |
| 2$^{nd}$ Layer | 0 | 200 | 0 |
| 3$^{rd}$ Layer | 180 | 200 | 90 |

As shown in Table 4, only the third layer, which was the lower-most layer, absorbed the urine, and the first and the second layers did not absorb urine. Also, according to visual observation, while absorption took place uniformly in nearly the entire surface area of the third layer, no wetting was observed in the first and second layers.

After the first urination, the third layer of the absorber was removed from the housing for the absorber units. At this time, the first layer and the second layer remained covered with the guide sheet in the housing for the absorber units. In other words, the removal of the third layer of the absorber was carried out easily, without any problems.

The results after the second urination of Example 4 are shown in Table 5.

TABLE 5

| Layer | The 1$^{st}$ Actual Amount Absorbed (mL) | The 2$^{nd}$ Actual Amount Absorbed (mL) | Designed Absorption Amount (mL) | Rate of Utilization (%) |
|---|---|---|---|---|
| 1$^{st}$ Layer | 0 | 10 | 200 | 5 |
| 2$^{nd}$ Layer | 0 | 210 | 200 | 105 |

As shown in Table 5, the second layer, which was the lower-most layer, absorbed the urine almost to the limit of its absorbing capacity, and the first layer absorbed the amount which was not absorbed by the second layer.

The second layer of the absorber was removed after the second urination. The removal of the second layer also was carried out easily, without any problems.

The results after the first urination of Comparative Example 4 are shown in Table 6.

TABLE 6

| Layer | Actual Amount Absorbed (mL) | Designed Absorption Amount (mL) | Rate of Utilization (%) |
|---|---|---|---|
| 1$^{st}$ Layer | 95 | 200 | 47.5 |
| 2$^{nd}$ Layer | 65 | 200 | 32.5 |
| 3$^{rd}$ Layer | 35 | 200 | 17.5 |

As shown in Table 6, the first layer, which was the upper-most layer, absorbed about one half of the urine, and the second and the third layers also absorbed some urine. Furthermore, according to the visual observation, absorption took place on the entire surface, except for about ⅓ of the total area located on the front side. The thickness in the back side, however, was large, more precisely it was 1.5 cm. This was assumed to be the result of temporarily retaining the urine which was not absorbed first and then gradually absorbing it later. In the second layer, absorption took place to a level that thickened the absorber to about 1cm, in an area equivalent to about ⅓ of the total area located on the back side. Furthermore, some portions on the front side were assumed to be penetrated with urine from the first layer. In the third layer, absorption took place to a level that thickened the absorber to about 1 cm, in an area equivalent to about ⅓ of the total area located on the back side.

After the first urination, the first layer of the absorber was removed from the housing for the absorber units. At this time, because it was impossible to remove the first layer only, and the second layer and the third layer also came out, the first layer was separated from the rest and the second and the third layers were put back to the housing for the absorber units. In other words, the removal of the first layer was difficult.

The results after the second urination in Comparative Example 4 are shown in Table 7.

TABLE 7

| Layer | The 1$^{st}$ Actual Amount Absorbed (mL) | The 2$^{nd}$ Actual Amount Absorbed (mL) | Designed Absorption Amount (mL) | Rate of Utilization (%) |
|---|---|---|---|---|
| 2$^{nd}$ Layer | 65 | 125 | 200 | 95 |
| 3$^{rd}$ Layer | 35 | 75 | 200 | 55 |

As shown in Table 7, the second layer, which was the upper-most layer, absorbed about ⅔ of the urine and the third layer also absorbed some.

After the second urination, the second layer of the absorber was removed from the housing for the absorber units, but the removal of the second layer also was difficult.

The results after the first urination in Comparative Example 5 are shown in Table 8.

TABLE 8

| Layer | Actual Amount Absorbed (mL) | Designed Absorption Amount (mL) | Rate of Utilization (%) |
|---|---|---|---|
| 1$^{st}$ Layer | 60 | 200 | 30 |
| 2$^{nd}$ Layer | 60 | 200 | 30 |
| 3$^{rd}$ Layer | 50 | 200 | 25 |

As shown in Table 8, absorption took place almost uniformly in the first through third layers. Therefore, continued use by removing one of the layers was unlikely. Because of this, the second urination was not performed.

Note that the "Designed Absorption Amount" in Tables 4 through 8 represents each absorber's absorbing capacity of the sodium chloride solution of 0.9 wt % under a load of 0.5 psi (3.448×10$^3$ Pa).

As evidenced by the above Examples, one of the preferred embodiments of the absorbent product is that its re-wet amount measured under a load of 0.1 psi, 5 minutes later from the beginning of the absorption, after having a sodium chloride solution of 0.9 wt % in the amount equivalent to 50% of the absorbing capacity of the absorber absorbed in the absorber at 25% under no load, is 5 mL or less, or more preferably 2 mL or less.

Furthermore, one of the preferred embodiments of the absorbent product is that the absorber's absorbing capacity of sodium chloride solution of 0.9 wt % is 300 mL or more, and when saline is added to be absorbed by the absorber in the amount of 100 mL each time in three separate additions under no load in every 10 minutes, an average re-wet amount after three additions is 5 mL or less, and the standard deviation of the re-wet amount is 3 mL or less; and when saline is added to be absorbed by the absorber in the amount of 100 mL each time in three separate additions under a load of 0.1 psi in every 10 minutes, the mean absorption time of the three additions is 30 seconds or less, and the standard deviation of the absorption time is 2 seconds or less.

3. Characteristics of the Absorbent Products, Including the Backflow Prevention Sheet The re-wet amount in the feces-disposing portion of the absorbent product without a backflow prevention sheet as shown in FIG. 21 and the re-wet amount in the feces-disposing portion of the absorbent product with a backflow prevention sheet as shown in FIG. 22 were compared. Both of these absorbent products were for both urine- and feces-disposing. Widths in the left-to-right direction of the surface sheet 10, absorber 14, guide sheet 22 and the backflow prevention sheet 38 were the same in these absorbent products.

As shown in FIG. 29, a liquid-supplying plate 92, comprising a cylindrical liquid-supplying portion with 2.0 cm inside diameter, and a weight 94 positioned in the periphery of the liquid-supplying portion, was placed on a urine-disposing portion 34 of the absorbent product 14, and a load of 0.1 psi was applied. At the same time, a paper filter 96 whose weight was measured beforehand was placed on a feces-disposing portion 36 of the absorbent product 14, and further an acrylic plate 98 was placed on it, and furthermore a weight was put on top of it to apply a load of 0.1 psi on it.

100 mL sodium chloride solution of 0.9 wt % was supplied to the liquid-supplying portion, and 3 minutes later from the beginning of the supplying of the liquid, the paper filter was removed to be weighed. This exercise was repeated three times in such a manner that supplies of the liquid began in every 10 minutes.

The results are shown in Table 9.

TABLE 9

| | | Without Backflow Prevention Sheet | With Backflow Prevention Sheet |
|---|---|---|---|
| Re-wet Amount at Feces-disposing Portion (mL) | $1^{st}$ Time | 0.5 | 0.0 |
| | $2^{nd}$ Time | 1.8 | 0.1 |
| | $3^{rd}$ Time | 2.9 | 0.7 |

As shown in Table 9, the re-wet amount at the feces-disposing portion was extremely small when the absorbent product for both urine- and feces-disposing included the backflow prevention sheet.

INDUSTRIAL APPLICABILITY

The absorbent product is suitable for use as a baby diaper, adult incontinence diaper, sanitary napkin for women, etc. because it is capable of preventing the absorbing rate of discharged liquid from significantly lowering with the elapse of time, and has a very small re-wet amount.

What is claimed is:

1. An absorbent product, comprising:
   a surface sheet which is liquid-impermeable;
   a back sheet which is liquid-impermeable positioned under the surface sheet; and
   an absorber including super absorbent polymer, the absorber being positioned between a lower side of the surface sheet and the back sheet, wherein
   the surface sheet fully covers in a lateral direction, and partially or fully covers in a longitudinal direction, an upper surface of the absorber, the longitudinal direction being a direction from front to back of a wearer's body when the absorbent product is worn and perpendicular to the lateral direction,
   the back sheet fully covers a lower surface of the absorber in the longitudinal direction and the lateral direction, and includes a left wall and a right wall, the left wall and the right wall extending along a left side and a right side of the absorber respectively, and exceeding the surface sheet in a lamination direction in which the absorber and the surface sheet are laminated on the back sheet,
   a set of flow passages formed in the longitudinal direction beginning an upper side of the surface sheet where a discharged liquid is supplied from the wearer's body, each flow passage exceeding each lateral end of the surface sheet and extending along a space between the left and right walls of the back sheet and the left and right sides of the absorber respectively, and
   each flow passage is provided such that at least a part of the discharged liquid flows off from the surface sheet into at least one of the flow passages, toward the back sheet and moves between the back sheet and the absorber.

2. The absorbent product according to claim 1, wherein a liquid-permeable guide sheet is laminated to at least a portion of the surface of an upper side of the surface sheet.

3. The absorbent product according to claim 2, further comprising:
   an absorbent product main body that can form an internal space to contain a wearer's objective region when worn; and
   a housing for an absorber unit adjacent to the absorbent product main body, continued to the internal space, wherein the housing contains the back sheet on an inner wall thereof, and
   wherein an absorber unit including at least the surface sheet and the absorber is removably received by the housing for the absorber unit.

4. The absorbent product according to claim 2, further comprising:
   an absorbent product main body that can form an internal space to contain a wearer's objective region when worn; and
   a housing for an absorber adjacent to the absorbent product main body, extending to the internal space, wherein the housing contains the back sheet on an inner wall thereof, and
   wherein the absorber is removably received by the housing, and at least a portion of the surface sheet is located between the absorbent product main body and the housing for the absorber.

5. The absorbent product according to claim 3, wherein the guide sheet is included at least in a portion between the internal space of the absorbent product main body and the housing for the absorber unit.

6. The absorbent product according to claim 4, wherein substantially all of the guide sheet is laminated on a surface of the upper side of the surface sheet.

7. The absorbent product according to claim 1, wherein at least one of the flow passages are provided in at least one of both front and back ends of the absorber, and in the center of the absorber.

8. The absorbent product according to claim 1, wherein the surface sheet is composed of a synthetic resin film which is a single layer.

9. The absorbent product according to claim 1, wherein the surface sheet is composed of a laminate of a synthetic resin film and a nonwoven fabric provided on a surface of an upper side of the synthetic resin film.

10. The absorbent product according to claim 8, wherein the synthetic resin film has concave and convex portions that constitute the flow passages.

11. The absorbent product according to claim 1, wherein the surface sheet is positioned such that a portion of the upper surface of the absorber is exposed.

12. The absorbent product according to claim 2, wherein the guide sheet covers at least a portion of the lateral sides of the absorber directly or over the surface sheet.

13. The absorbent product according to claim 2, wherein the guide sheet has concave and convex portions that constitute the flow passages and has apertures in some of or in all of the convex portions.

14. The absorbent product according to claim 1, wherein a skin-contactable sheet composed of liquid-permeable nonwoven fabric is laminated to at least a portion of the upper side of the surface sheet.

15. The absorbent product according to claim 1, wherein the back sheet is composed of a synthetic resin film.

16. The absorbent product according to claim 15, wherein the synthetic resin film that constitutes the back sheet has air-permeability.

17. The absorbent product according to claim 1, wherein the back sheet is composed of a laminate of a synthetic resin film and a nonwoven fabric provided on the surface of the lower side of the synthetic resin film.

18. The absorbent product according to claim 17, wherein both the synthetic resin film and the nonwoven fabric that constitute the back sheet have air-permeability.

19. The absorbent product according to claim 17, wherein the synthetic resin film that constitutes the back sheet has concave and convex portions and has apertures in some of or in all of the convex portions, and the nonwoven fabric that constitutes the back sheet is a water-resistant laminate of at least two layers, containing at least one layer of a spunbond nonwoven fabric and one layer or more than one layer of meltblown nonwoven fabric.

20. The absorbent product according to claim 15, wherein the synthetic resin film that constitutes the back sheet has concave and convex portions constituting a liquid trap portion on a surface of an upper side thereof.

21. The absorbent product according to claim 1, wherein the absorber is composed of a mixture of the super absorbent polymer and fluffy pulp wrapped with a liquid-permeable core-wrapping sheet.

22. The absorbent product according to claim 1, wherein the absorber has two layers of liquid-permeable nonwoven fabrics and the super absorbent polymer is inserted in between the two layers.

23. The absorbent product according to claim 1, wherein the absorber includes the super absorbent polymer supported by means of coating on a liquid-permeable nonwoven fabric.

24. The absorbent product according to claim 1, wherein a content of the super absorbent polymer in the absorber is 50 wt % or more.

25. The absorbent product according to claim 1, further comprising:
an absorbent product main body that can form an internal space to contain a wearer's objective region when worn;
a housing for an absorber unit adjacent to the absorbent product main body, continued to the internal space, wherein the housing contains the back sheet on an inner wall thereof; and
an absorber unit structured by combining at least the surface sheet and the absorber, the absorber unit being removably received by the housing for the absorber unit.

26. The absorbent product according to claim 25, wherein a liquid-permeable skin-contactable sheet is included at least in a portion between the internal space of the absorbent product main body and the housing for the absorber unit.

27. The absorbent product according to claim 25, wherein the housing for the absorber unit includes a plurality of the absorber units, the absorber units being laminated.

28. The absorbent product according to claim 1, further comprising:
an absorbent product main body that can form an internal space to contain a wearer's objective region when worn; and
a housing for an absorber adjacent to the absorbent product main body, continued to the internal space, wherein the housing contains the back sheet on an inner wall thereof, and
wherein an absorber is removably received by the housing for the absorber; and,
wherein the surface sheet is included at least in a portion between the internal space of the absorbent product main body and the housing for the absorber.

29. The absorbent product according to claim 28, wherein a liquid-permeable skin-contactable sheet is provided at least on a portion of a surface of the upper side of the surface sheet.

30. The absorbent product according to claim 28, wherein the housing for the absorber includes a plurality of the absorbers, the absorbers being laminated.

31. The absorbent product according to claim 1, wherein a urine-disposing portion extending from a center to a front section and a feces-disposing portion extending from the center to a back section are provided and the surface sheet is provided only at the urine-disposing portion.

32. The absorbent product according to claim 31, wherein a liquid-impermeable back-flow preventing sheet is included inside at least one of an on an upper surface of the absorber, at least at the feces-disposing portion.

33. The absorbent product according to claim 1, wherein a re-wet amount measured under a load of 0.1 psi (5 minutes after the beginning of the absorption to allow a sodium chloride solution of 0.9 wt % in the amount equivalent to 50% of the absorbing capacity of the absorber to be absorbed in the absorber at 25° C. under no load) is 5 mL or less.

34. The absorbent product according to claim 33, wherein the re-wet amount is 2 mL or less.

35. The absorbent product according to claim 1,
wherein the absorber's absorbing capacity of sodium chloride solution of 0.9 wt % is 300 mL or more, and
an average re-wet amount after three additions of 100 mL of saline under no load, one said addition every 10 minutes, is 5 mL or less; and
when saline is added to be absorbed by the absorber in the amount of 100 mL each time in three separate additions under a load of 0.1 psi in every 10 minutes, the mean absorption time of the three additions is 30 seconds or less,
and the standard deviation of the absorption time is 2 seconds or less.

36. The absorbent product according to claim 9, wherein the synthetic resin film has concave and convex portions that constitutes at least one of the flow passages.

37. The absorbent product according to claim 2, wherein a skin-contactable sheet composed of liquid-permeable nonwoven fabric is laminated to at least a portion of at least one of a surface of the upper side of the surface sheet and an upper side of a surface of the guide sheet.

38. The absorbent product according to claim 6, wherein a liquid-permeable skin-contactable sheet is provided at least on a portion of at least one of the surface of the upper side of the surface sheet and the surface of the upper side of the guide sheet.

* * * * *